(12) United States Patent
Freeman et al.

(10) Patent No.: US 10,137,265 B2
(45) Date of Patent: *Nov. 27, 2018

(54) SYSTEMS AND METHODS FOR WIRELESS FEEDBACK DURING VENTILATION

(75) Inventors: Gary A. Freeman, Newton Center, MA (US); Annemarie Silver, Bedford, MA (US); Ulrich Herken, Medford, MA (US); Jon P. Cloutier, Broomfield, CO (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 1288 days.

This patent is subject to a terminal disclaimer.

(21) Appl. No.: 13/473,002

(22) Filed: May 16, 2012

(65) Prior Publication Data

US 2012/0302910 A1 Nov. 29, 2012

Related U.S. Application Data

(60) Provisional application No. 61/489,086, filed on May 23, 2011.

(51) Int. Cl.
*A61B 5/08* (2006.01)
*A61M 16/00* (2006.01)
(Continued)

(52) U.S. Cl.
CPC .... *A61M 16/0084* (2014.02); *A61M 16/0003* (2014.02); *A61M 16/0069* (2014.02); *A61M 16/021* (2017.08); *A61N 1/3987* (2013.01); *A61H 31/00* (2013.01); *A61H 31/005* (2013.01); *A61H 2201/5071* (2013.01); *A61H 2201/5084* (2013.01); *A61H 2230/205* (2013.01); *A61H 2230/207* (2013.01); *A61H 2230/42* (2013.01); *A61H 2230/80* (2013.01); *A61M 16/0078* (2013.01); *A61M 16/0858* (2014.02); *A61M 2016/003* (2013.01); *A61M 2016/0024* (2013.01); *A61M 2016/0027* (2013.01); *A61M 2016/0036* (2013.01);
(Continued)

(58) Field of Classification Search
USPC ...................................... 600/538; 128/205.13
See application file for complete search history.

(56) References Cited

U.S. PATENT DOCUMENTS 3,991,304 A 11/1976 Hillsman
4,481,944 A * 11/1984 Bunnell ................ A61M 16/00
128/203.17

(Continued)

FOREIGN PATENT DOCUMENTS

CN 1613097 A 5/2005
CN 101296730 A 10/2008
(Continued)

OTHER PUBLICATIONS

Hightower, et al., Decay in Quality of Chest Compressions Over Time, 26 Ann. Emerg. Med. 300 (Sep. 1995) (Hightower).*
(Continued)

*Primary Examiner* — Christian Jang
*Assistant Examiner* — Mitchell E Alter
(74) *Attorney, Agent, or Firm* — The Webb Law Firm

(57) ABSTRACT

Systems and methods regarding ventilation of a patient, such as a victim at the scene of an emergency are described herein.

58 Claims, 18 Drawing Sheets

(51) Int. Cl.
*A61N 1/39* (2006.01)
*A61H 31/00* (2006.01)
*A61M 16/08* (2006.01)

(52) U.S. Cl.
CPC ... *A61M 2205/054* (2013.01); *A61M 2205/15* (2013.01); *A61M 2205/332* (2013.01); *A61M 2205/3569* (2013.01); *A61M 2205/3592* (2013.01); *A61M 2205/505* (2013.01); *A61M 2205/581* (2013.01); *A61M 2205/583* (2013.01); *A61M 2205/587* (2013.01); *A61M 2230/432* (2013.01); *A61M 2230/46* (2013.01)

(56) References Cited

U.S. PATENT DOCUMENTS

| | | | |
|---|---|---|---|
| 5,327,887 A * | 7/1994 | Nowakowski | A61H 31/006 128/202.13 |
| 6,269,267 B1 | 7/2001 | Bardy et al. | |
| 6,273,088 B1 | 8/2001 | Hillsman | |
| 6,980,112 B2 | 12/2005 | Nee | |
| 7,242,979 B1 | 7/2007 | Kelly et al. | |
| 2002/0133197 A1 | 9/2002 | Snyder et al. | |
| 2002/0139369 A1* | 10/2002 | Maguire | A61M 16/0075 128/205.13 |
| 2003/0089371 A1* | 5/2003 | Robertson | A61M 16/0488 128/201.26 |
| 2004/0016434 A1* | 1/2004 | Jamison | A61B 5/0836 128/204.23 |
| 2004/0099267 A1* | 5/2004 | Ahlmen | A61M 16/0051 128/203.12 |
| 2004/0162587 A1 | 8/2004 | Hampton et al. | |
| 2004/0254773 A1* | 12/2004 | Zhang | A61B 5/1135 703/11 |
| 2005/0061315 A1 | 3/2005 | Lee et al. | |
| 2005/0085799 A1 | 4/2005 | Luria et al. | |
| 2005/0101889 A1* | 5/2005 | Freeman | A61B 5/04017 601/41 |
| 2005/0119586 A1* | 6/2005 | Coyle | A61B 5/0806 600/538 |
| 2006/0129191 A1 | 6/2006 | Sullivan et al. | |
| 2007/0017521 A1 | 1/2007 | Ben et al. | |
| 2007/0032830 A1 | 2/2007 | Bowers | |
| 2007/0060785 A1* | 3/2007 | Freeman | A61H 31/00 600/16 |
| 2007/0068528 A1* | 3/2007 | Bohm | A61B 5/085 128/204.23 |
| 2007/0162076 A1 | 7/2007 | Tan et al. | |
| 2007/0169779 A1 | 7/2007 | Freeman | |
| 2007/0219588 A1* | 9/2007 | Freeman | A61H 31/005 607/5 |
| 2008/0027338 A1 | 1/2008 | Lu et al. | |
| 2008/0053445 A1 | 3/2008 | Kroupa et al. | |
| 2008/0139948 A1 | 6/2008 | Stahmann et al. | |
| 2008/0214948 A1 | 9/2008 | Myklebust et al. | |
| 2008/0236585 A1* | 10/2008 | Parker | A61M 16/0078 128/205.23 |
| 2008/0295839 A1* | 12/2008 | Habashi | A61M 16/0051 128/204.22 |
| 2009/0012395 A1* | 1/2009 | Reynolds | A61B 5/0806 600/437 |
| 2009/0024175 A1* | 1/2009 | Freeman | A61H 31/00 607/6 |
| 2009/0151724 A1* | 6/2009 | Wondka | A61M 16/0096 128/204.23 |
| 2009/0163838 A1 | 6/2009 | Hecox et al. | |
| 2009/0320836 A1 | 12/2009 | Baker, Jr. | |
| 2010/0018530 A1 | 1/2010 | Schindhelm et al. | |
| 2010/0256539 A1 | 10/2010 | Strand et al. | |
| 2011/0082510 A1 | 4/2011 | Sullivan | |
| 2011/0197885 A1* | 8/2011 | Wondka | A61B 5/03 128/204.22 |
| 2011/0202100 A1 | 8/2011 | Tan et al. | |
| 2011/0284004 A1* | 11/2011 | Silver | A61B 5/087 128/205.13 |
| 2012/0000464 A1 | 1/2012 | Gajic et al. | |
| 2013/0009783 A1 | 1/2013 | Tran | |
| 2013/0030173 A1 | 1/2013 | Wang et al. | |

FOREIGN PATENT DOCUMENTS

| | | |
|---|---|---|
| CN | 101626797 A | 1/2010 |
| EP | 1834622 | 9/2007 |
| GB | 2446124 | 8/2008 |
| JP | 2007195977 A | 8/2007 |
| JP | 2007244879 A | 9/2007 |
| JP | 2010502285 A | 1/2010 |
| WO | 02078775 A2 | 10/2002 |
| WO | WO2008/027418 | 3/2008 |
| WO | WO2010/059049 | 5/2010 |
| WO | WO 2010/059049 A2 * | 5/2010 |

OTHER PUBLICATIONS

International Search Report & Written Opinion, PCT/US2012/038076, dated Oct. 29, 2012, 17 pages.
Invitation to Pay Additional Fees and, Where Applicable, Protest Fee, PCT/US2012/038076, dated Aug. 13, 2012, 4 pages.
Sullivan et al.; "How Much Can Hands-off Time Be Reduced by Performing Rhythm Analysis During CPR?"; American Heart Association Abstract P176; Circulation 2009; 120:S1479.
Aase et al.; "CPR Artifact Removal from Human ECG Using Optimal Multichannel Filtering"; IEEE Transactions on Biomedical Engineering; Nov. 2000; pp. 1440-1449; vol. 47, No. 11.
For p. S1455; how to list.
Li et al.; "Identifying Potentially Shockable Rhythms Without Interrupting Cardiopulmonary Resuscitation"; Crit Care Med; 2008; pp. 198-203; vol. 36, No. 1.
Lloyd et al.; "Hands-On Defibrillation: An Analysis of Electrical Current Flow Through Rescuers in Direct Contact with Patients During Biphasic External defibrillation"; Circulation; May 13, 2008; pp. 2510-2514.
Povoas et al.; "Predicting the Success of Defibrillation by Electrocardiographic Analysis"; Resuscitation; 2002, pp. 77-82; vol. 53.
Circulation; Journal of the American Heart Association; Nov. 3, 2009; 3 pages; vol. 120, No. 18.
deGauna et al.; "A Method to Remove CPR Artefacts from Human ECG Using Only the Recorded ECG"; Resuscitation; 2008; pp. 271-278; vol. 76.
For p. S1479 how to list.
Yu et al.; "The Resuscitation Blanket: A Useful Tool for 'Hands-on' Defibrillation"; Resuscitation; 2010; pp. 230-235; vol. 81.

* cited by examiner

SYSTEMS AND METHODS FOR WIRELESS FEEDBACK DURING VENTILATION

CROSS-REFERENCE TO RELATED APPLICATIONS

This application claims the benefit under 35 U.S.C. § 119(e) of U.S. Provisional Application Ser. No. 61/489,086 filed May 23, 2011. All subject matter set forth in the above referenced application is hereby incorporated by reference into the present application as if fully set forth herein.

TECHNICAL FIELD

This document relates to systems and methods for regarding ventilation of a patient, such as a victim at the scene of an emergency.

BACKGROUND

Resuscitation treatments for patients suffering from cardiac arrest generally include clearing and opening the patient's airway, providing rescue breathing for the patient, and applying chest compressions to provide blood flow to the victim's heart, brain and other vital organs. If the patient has a shockable heart rhythm, resuscitation also may include defibrillation therapy. Such treatment may include basic life support (BLS), which involves initial assessment; airway maintenance; expired air ventilation (rescue breathing); and chest compression. When all these elements are combined, the term cardiopulmonary resuscitation (CPR) is used. Relatively untrained rescuers, such as laypeople, may provide BLS, while trained rescuers such as physicians or emergency medical technicians (EMTs) may provide advanced life support (ALS), which may additionally involve, among other things, cardiac monitoring, intravenous cannulation (IV), intraosseous (IO) access and intraosseous infusion, surgical cricothyrotomy, needle cricothyrotomy, and advanced medication administration through parental and enteral routes.

Ventilation in various instances may involve rescue breathing, or more commonly, bag or bag-valve-mask ventilation for ALS, which involves placing a mask in a seal over a patient's face and forcing air into the patient's lungs by repeatedly compressing and expanding a flexible device that is attached to the mask. Such ventilation may be performed in time-wise coordination with chest compressions and with defibrillation shocks delivered by a defibrillator, such as a portable defibrillator in the form of an automatic external defibrillator (AED) or other types of defibrillators. The chest compression can be automatically coordinated by the defibrillator, such as by the provision of an accelerometer positioned relative to the defibrillator electrodes on a patient's chest so that the accelerometer can be used to provide a rescuer with feedback if they are compressing too hard or too soft, and too fast or too slow, as compared to set standards and protocols.

SUMMARY

This document describes systems and techniques that may be used to monitor ventilation to a patient. In one example, a ventilation monitor is placed in or on a manual ventilation assembly in the form of a ventilation bag and mask. The ventilation monitor may include a ventilation sensor for sensing a direction of ventilation (inhalation or exhalation of the patient) and may also include a sensors for sensing the volume of the patient's ventilation, pressure and/or gas composition such as $CO_2$ percentage.

In some aspects, a medical system includes a manual patient ventilation unit defining an airflow path, the unit arranged so that when the unit is applied to a patient, the airflow path is in fluid communication with the patient's airway, the patient ventilation unit comprising a ventilation bag configured to enable manual ventilation of the patient by a rescuer. The system also includes an airflow sensor in the airflow path positioned to sense the presence of ventilation airflow and measure a gas flow rate in the airflow path and a pressure sensor in the airflow path positioned to sense gas pressure in the airflow path. The system also includes a processor arranged to receive data generated by the airflow sensor and the pressure sensor and determine one or more ventilation quality parameters based at least in part on a gas flow volume calculated based on the sensed gas flow rate and gas pressures and a feedback unit to provide feedback to a rescuer based on the one or more ventilation quality parameters.

Embodiments can include one or more of the following.

The system can also include circuitry configured for delivery of electromagnetic stimulation to the patient.

The ventilation bag can include a flexible reservoir containing ventilatory gases configured to enable manual ventilation of the patient by a rescuer squeezing the flexible reservoir.

The ventilation bag can be configured to enable manual ventilation of the patient by a rescuer pressing a switch of an electromechanically-controlled ventilator.

The system can also include a sensor configured to detect and measure a quality of chest compressions.

The one or more ventilation quality parameters can include an indicator indicative of a ventilation being delivered during a compression cycle.

The ventilation quality parameters can include one or more of tidal volume, minute volume, end-inspiratory and maximum ventilation pressure.

The ventilation quality parameters can include instantaneous lung compliance measurements.

The processor can be further configured to detect at least one of the following conditions: barotrauma, hemothorax, pneumothorax, intubation in the mainstem, flail chest, or pediatric lung distension based at least in part on the lung compliance measurements.

The system can also include a capnometer in the airflow path positioned to sense the concentration of $CO_2$ in the airflow path.

The system can also include an oxygen sensor in the airflow path positioned to sense the concentration of $O_2$ in the airflow path.

The processor can be configured to compute end-tidal $CO_2$ values and the feedback unit can be configured to provide an indication to increase ventilation if the end-tidal $CO_2$ value is outside of a first range and to decrease ventilation if the end-tidal $CO_2$ value is outside of a second range.

The processor can be further configured to compute volumetric $CO_2$ values and the feedback unit can be configured to provide an indication to increase ventilation if the volumetric $CO_2$ value is outside of a first range and to decrease ventilation if the volumetric $CO_2$ value is outside of a second range The processor can be configured to compute lung compliance.

The feedback unit can be configured to provide feedback related to tidal volume.

The processor can be configured to compute a difference in in-flow volume and out-flow volume and the feedback unit can be configured to provide feedback related one or more of ventilation release and ventilation seal.

The processor can be configured to identify conditions when a negative pressure occurs during in-flow of air and the feedback unit can be configured to provide feedback regarding the existence of a spontaneous breath when a negative pressure occurs during in-flow of air.

The feedback can include feedback that communicates to the rescuer an appropriate rate for providing ventilation to the patient.

The feedback comprises feedback that communicates to the rescuer an appropriate volume for providing ventilation to the patient.

The feedback unit can be a visual feedback mechanism for providing information to a rescuer regarding delivery of ventilation comprising a plurality of lights arranged to indicate, based on which lights of the plurality of lights are activated, whether excessive ventilation, too little ventilation, or an appropriate amount of ventilation is being provided to the victim.

The feedback unit can be configured to provide an instruction pertaining to varying the ventilation rate.

The feedback unit can be configured to provide an instruction pertaining to varying the delivered tidal volume.

The feedback unit can be a visual feedback mechanism for providing information to a rescuer regarding delivery of ventilation comprising a ventilation timer providing information about respiratory rate.

The feedback unit can be a visual feedback mechanism for providing information to a rescuer regarding delivery of ventilation comprising a ventilation timer providing information about elapsed time between ventilation events.

The feedback unit can be a device configured to form audible prompts and the feedback comprises audible prompts.

The feedback unit can be a device configured to form audible prompts and the feedback comprises verbal instructions.

The feedback unit can be a device configured to form audible prompts and the feedback comprises one or more tones.

The feedback unit can be a graphical display and the feedback comprises visual feedback.

The feedback unit can be a graphical display and the feedback comprises a visual representation of a shape with demarcations indicating specific tidal volume values, wherein the volume fills during the ventilation.

The visual representation can include a visual marker indicative of a target tidal volume.

The processor can be further configured to determine compliance features and determine a patient state based on the compliance features.

The patient state can include a state selected from the group consisting of barotraumas, hemothorax, pneumothorax, intubation in mainstem, flail chest, and pediatric lung overdistension.

The system can also include a sensor configured to detect manual or mechanical CPR compressions.

The sensor can be configured to detect manual or mechanical CPR compressions comprises an accelerometer.

The sensor can be configured to detect manual or mechanical CPR compressions comprises a pressure sensor.

The processor can be further configured to receive data from the sensor configured to detect manual or mechanical CPR compressions and determine whether a timing for a ventilation overlaps with a timing for a CPR compression cycle.

The processor can be further configured to detect a mask leak.

The processor can be further configured to compare pressure data from the pressure sensor and flow data from the airflow sensor at multiple points in time to compute an estimate of compliance.

The processor can be further configured to detect overdistension of lungs during pediatric ventilation based on the estimate of compliance and the feedback unit is further configured to provide information related to for appropriate lung ventilation volume for a pediatric patient.

The processor can be configured to detect a spontaneous breath based on information related to a negative pressure combined with inspiratory flow.

The feedback unit can be configured to provide a message indicating potential return of spontaneous circulation (ROSC) based on the detection of a spontaneous breath.

The processor can be further configured to generate an estimate of lung volume, generate an estimate of a thoracic state impedance based on the estimate of lung volume, provide the estimate of thoracic state impedance to an adaptive filter, and filter ventilation-induced artifacts in the transthoracic impedance signal to generate an estimate of the impedance changes induced by cardiac output.

The feedback unit can be configured to provide a simultaneous display of flow rate and volume.

The feedback can be a graphical plot.

The feedback can be side-by-side numerics.

The feedback can include spirometery data for one or more of oxygen, carbon dioxide, overall gas volume and rate.

The feedback can include a value indicative of a measure of the squareness of a spirometry curve.

The processor can be further configured to receive information related to two or more of a patient's height, girth, weight and gender and calculate an estimate thoracic volume based on the two or more of the patient's height, girth, weight and gender.

The processor can be further configured to receive the information related to two or more of the patient's height, girth, weight and gender from a tablet PC.

The processor can be further configured to receive the information related to two or more of the patient's height, girth, weight and gender from an accelerometer.

The processor can be further configured to receive the information related to two or more of the patient's height, girth, weight and gender from an automatic defibrillation and compression device configured to obtain a measure of patient circumference.

The processor can be further configured to calculate the estimate thoracic volume based on a measured ventilation tidal volume and an instantaneous lung volume.

The patient ventilation unit can include a handheld breathing tube.

The patient ventilation unit can include a mouthguard configured to fit between the patient's lips and teeth and to provide a seal between the ventilation unit and the patient.

The patient ventilation unit can include a mask that seals to and fits over a lower portion of the patient's face.

The airflow sensor can be a differential pressure sensor.

In some additional aspects, a system includes an airflow sensor in the airflow path positioned to sense the presence of ventilation airflow and measure gas flow rates in the airflow path of a conscious patient experiencing dyspnea; and a pressure sensor in the airflow path positioned to sense gas pressure in the airflow path of the conscious patient experiencing dyspnea. The system also includes a processor arranged to receive data generated by the airflow sensor and the pressure sensor and determine one or more ventilation quality parameters requiring gas flow volume for their calculation, the one or more ventilation quality parameters including spirometric measurements. The system also includes circuitry configured for delivery of electromagnetic stimulation to the patient and a feedback unit configured to provide feedback to a rescuer based on the one or more ventilation quality parameters.

Embodiments can include one or more of the following.

The feedback unit can be configured to display the spirometric information as simultaneous display of flow rate and volume.

The feedback unit can be configured to display the spirometric information in the form of a graphical plot.

The feedback unit can be configured to display the spirometric information in the form of side-by-side numerics.

The spirometric information can include spirometric information for one or more of the following: oxygen, carbon dioxide, overall gas volume and rate.

The feedback unit can be configured to display a single value that provides a measure of the squareness of a spirometry curve based on the spirometric measurements.

The patient ventilation unit can include a handheld breathing tube.

The handheld breathing tube can include a gripping portion in the shape of a mouthguard.

The details of one or more embodiments are set forth in the accompanying drawings and the description below. Other features and advantages will be apparent from the description and drawings, and from the claims.

DETAILED DESCRIPTION

This document describes mechanisms by which various devices can interact in a life-saving situation to improve the care that a victim (which should be understood to be a person in need of CPR, ventilation, or related care that is typically provided by an emergency medical technician or physician, but may also be provided by lay responders in certain situations) receives in such a situation. In particular, this document describes a system in which a patient ventilation sensor communicates with one or more other portable medical devices so that a ventilation rate, and perhaps a ventilation volume, may be analyzed, and a provider of care to the victim may be instructed in how best to ventilate the victim. The instructions may be coordinated with instructions for giving chest compressions to the victim and for defibrillating the victim. As one example, instructions regarding how fast, and when, to provide chest compressions and ventilation may be provided in a properly coordinated manner. Also, as a battery charges for a defibrillation pulse, such timing may be adjusted so that chest compressions and ventilation are finished as the defibrillator reaches a fully charged state, so that a defibrillation pulse may be delivered immediately upon the unit becoming charged. Also, the charging rate of the unit may be changed based on the location that rescuers are currently at in a protocol, so that the charging can occur at a rate that the device is ready at the proper point, and the device may be charged more slowly than it might otherwise be charged, thus conserving battery power in the device.

Figure 1:
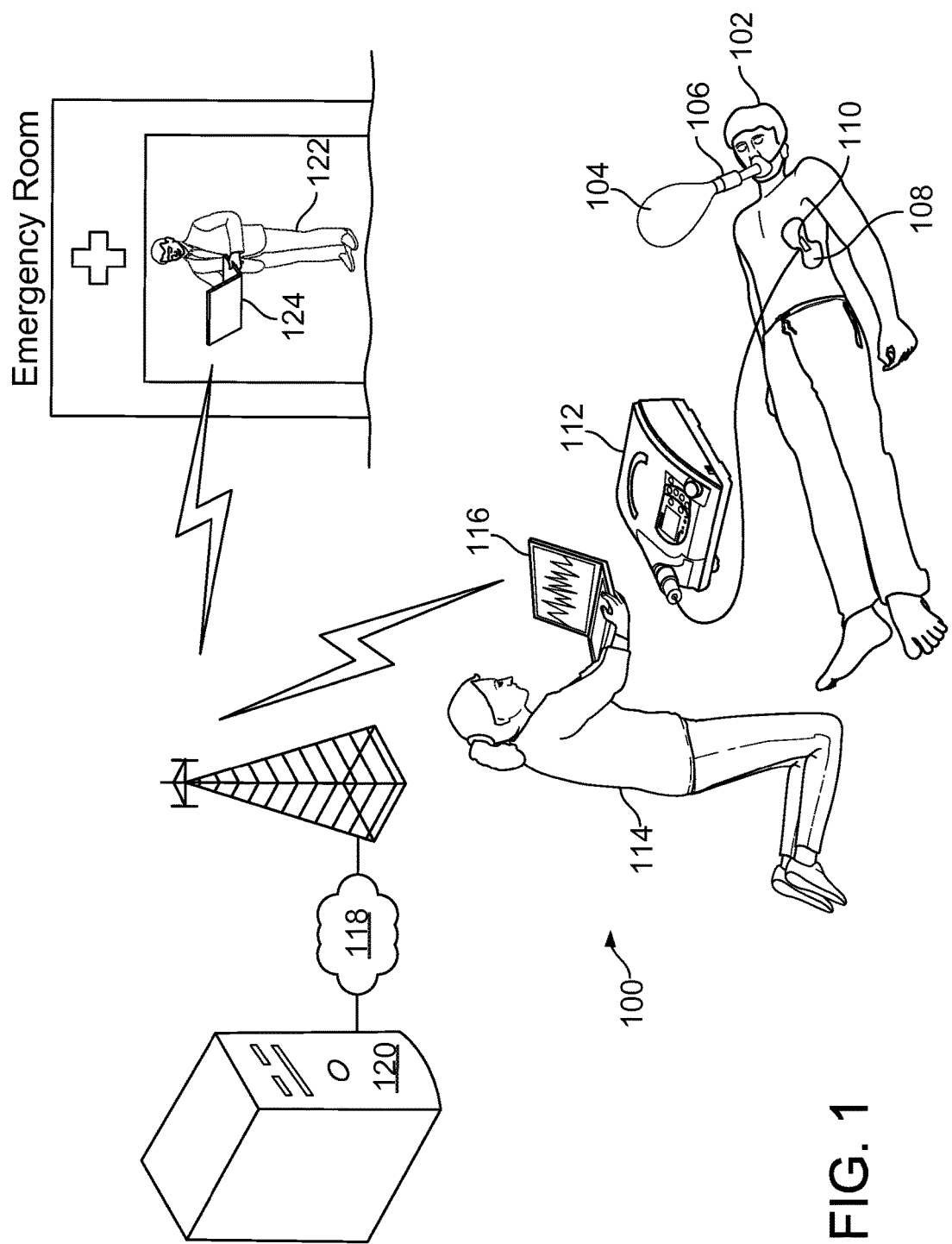
FIG. 1 shows a system for responding to an emergency medical condition.

FIG. 1 shows a system 100 for responding to an emergency medical condition. In general, system 100 includes various portable devices for monitoring on-site care given to a victim of an emergency situation, such as a victim 102 suffering from sudden cardiac arrest or a victim 102 at the scene of a traffic accident. The various devices may be provided by emergency medical technicians who arrive at the scene and who provide care for the victim 102, such as emergency medical technician 114. In this example, the emergency medical technician 114 has deployed several devices and is providing care to the victim 102. Although not shown, one or more other emergency medical technicians may be assisting and working in coordination with emergency medical technician 114 according to a defined protocol and training.

The emergency medical technician 114 in this example is interacting with a computing device in the form of a touchscreen tablet 116. The tablet 116 may include a graphical display by which to report information to the emergency medical technician 114, and may have an input mechanism such as a keyboard or a touchscreen by which the emergency medical technician 114 may enter data into the system 100. The tablet 116 may also include a wireless transceiver for communicating with a wireless network, such as a 3G or 4G chipset that permits long distance communication over cellular data networks, and further through the internet.

Separately, a portable defibrillator 112 is shown in a deployed state and is connected to the victim 102. In this example, electrodes 108 have been applied to the bare chest of the victim 102 and have been connected to the defibrillator 112, so that electrical shocking pulses may be provided to the electrodes in an effort to defibrillate the victim 102. The defibrillator 112 may take a variety of forms, such as the ZOLL MEDICAL R Series, E Series, or M Series defibrillators.

The assembly for the electrodes 108 includes a center portion at which an accelerometer assembly 110 is mounted. The accelerometer assembly 110 may include a housing inside which is mounted an accelerometer sensor configuration. The accelerometer assembly 110 may be positioned in a location where a rescuer is to place the palms of their hands when performing cardio pulmonary resuscitation (CPR) on the victim 102. As a result, the accelerometer assembly 110 may move with the victim's 102 chest and the rescuer's hands, and acceleration of such movement may be double-integrated to identify a vertical displacement of such motion.

The defibrillator 112 may, in response to receiving such information from the accelerometer assembly 112, provide feedback in a conventional and known manner to a rescuer, such as emergency medical technician 114. For example, the defibrillator 112 may generate a metronome to pace such a user in providing chest compressions. In addition, or alternatively, the defibrillator 112 may provide verbal instructions to the rescuer, such as by telling the rescuer that they are providing compressions too quickly or too slowly, or are pushing too hard or too soft, so as to encourage the rescuer to change their technique to bring it more in line with proper protocol—where the proper protocol may be a protocol generated by the system, but that is inconsistent with any published protocols.

The defibrillator 112 may communicate through a short range wireless data connection with the tablet 116, such as using BLUETOOTH technology. The defibrillator 112 can provide to the tablet 116 status information, such as information received through the electrode assembly 108, including ECG information for the victim 102. Also, the defibrillator 112 can send information about the performance of chest compressions, such as depth and rate information for the chest compressions. The tablet 116 may display such information (and also other information, such as information from the defibrillator regarding ETCO2 and SPO2) graphically for the emergency medical technician 114, and may also receive inputs from the emergency medical technician 114 to control the operation of the various mechanisms at an emergency site. For example, the emergency medical technician 114 may use the tablet 116 to change the manner in which the defibrillator 112 operates, such as by changing a charging voltage for the defibrillator 112.

Another electronic mechanism, in the form of a ventilation bag 104 is shown sealed around the mouth of the victim 102. The ventilation bag 104 may, for the most part, take a familiar form, and may include a flexible body structure that a rescuer may squeeze periodically to provide ventilation on the victim 102 when the victim 102 is not breathing sufficiently on his or her own.

Provided with the ventilation bag 104 is an airflow sensor 106. The airflow sensor 106 is located in a neck of the ventilation bag 104 near the mouthpiece or mask of the ventilation bag 104. The airflow sensor 106 may be configured to monitor the flow of air into and out of the patient's mouth, so as to identify a rate at which ventilation is occurring with the victim. In addition, in certain implementations, the airflow sensor 106 may be arranged to monitor a volume of airflow into and out of the victim 102.

In this example, the airflow sensor 106 is joined to a short-range wireless data transmitter or transceiver, such as a mechanism communicating via BLUETOOTH technology. As such, the airflow sensor 106 may communicate with the tablet 116, the defibrillator 112, or another computer or processor in a manner similar to the communication of the defibrillator 112 with the tablet 116. For example, the airflow sensor 106 may report information that enables the computation of a rate of ventilation, and in some circumstances a volume of ventilation, provided to the patient. The tablet 116, for example, may determine an appropriate provision of ventilation and compare it to the determine provision, and may provide feedback for a rescuer, either directly such as by showing the feedback on a screen of the tablet 116 or playing the feedback through an audio system of the tablet 116, or indirectly, by causing defibrillator 112 or airflow sensor 106 to provide such feedback. For example, defibrillator 112 or airflow sensor 106 may provide a metronome or verbal feedback telling a rescuer to squeeze the ventilation bag 104 harder or softer, or faster or slower. Also, the system 100 may provide the rescuer was an audible cue each time that the bag is to be squeezed and ventilation is to be provided to the victim 102.

Such feedback may occur in a variety of manners. For example, the feedback may be played on built-in loudspeakers mounted in any of tablet 116, defibrillator 112, or airflow sensor 106. Alternatively, or in addition, visual notifications may be provided on any combination of such units. Also, feedback may be provided to wireless headsets (or other form of personal device, such as a smartphone or similar device that each rescuer may use to obtain information and to enter data, and which may communicate wirelessly over a general network (e.g., WiFi or 3G/4G) or a small area network (e.g., BLUETOOTH) that are worn by each rescuer, and two channels of communication may be maintained, so that each rescuer receives instructions specific to their role, where one may have a role of operating the defibrillator 112, and the other may have the role of operating the ventilation bag 104. In this manner, the two rescuers may avoid being accidentally prompted, distracted, or confused by instructions that are not relevant to them.

A central server system 120 may communicate with the tablet 116 or other devices at the rescue scene over a wireless network and a network 118, which may include portions of the Internet (where data may be appropriately encrypted to protect privacy). The central server system 120 may be part of a larger system for a healthcare organization in which medical records are kept for various patients in the system. Information about the victim 102 may then be associated with an identification number or other identifier, and stored by the central server system 120 for later access. Where an identity of the victim 102 can be determined, the information may be stored with a pre-existing electronic medical record (EMR) for that victim 102. When the identity of the victim 102 cannot be determined, the information may be stored with a temporary identification number or identifier, which may be tied in the system to the particular rescue crew so that it may be conveniently located by other users of the system.

The information that is stored may be relevant information needed to determine the current status of the victim 102 and the care that has been provided to the victim 102 up to a certain point in time. For example, vital signs of the victim 102 may be constantly updated at the central server system 120 as additional information is received from the tablet 116.

Also, ECG data for the victim 102 may be uploaded to the central server system 120. Moreover, information about drugs provided to the victim may be stored. In addition, information from a dispatch center may also be stored on a central server system and accessed by various users such as rescuers. For example, a time at which a call came in may be stored, and rescuers (either manually or automatically through their portable computing devices) can use that time to determine a protocol for treating the patient (e.g., ventilation or chest compression needs may change depending on how long the victim has been in need of treatment).

Other users may then access the data in the central server system 120. For example, as shown here, an emergency room physician 122 is operating his or her own tablet 124 that communicates wirelessly, such as over a cellular data network. The physician 122 may have been notified that victim 102 will be arriving at the emergency room, and, in preparation, may be getting up-to-speed regarding the condition of the victim 102, and determining a best course of action to take as soon as the victim 102 arrives at the emergency room. As such, the physician 122 may review the data from central server system 120. In addition, the physician 122 may communicate by text, verbally, or in other manners with emergency medical technician 114. In doing so, the physician 122 may ask questions of the emergency medical technician 114 so that the physician 122 is better prepared when the victim 102 arrives at the emergency room. The physician 122 may also provide input to the emergency medical technician 114, such as by describing care that the emergency medical technician 114 should provide to the victim 102, such as in an ambulance on the way to the emergency room, so that emergency room personnel do not have to spend time performing such actions. Also, physicians could see aspects of a currently-operating protocol on the system, and could act to override the protocol, with or without the rescuers needing to know that such a change in the protocol has been made (e.g., their devices will just start instructing them according to the parameters for the manually revised protocol).

Where the published protocol is organized in a flowchart form, the flowchart may be displayed to a rescuer or a physician, and such user may drag portions of the flowchart to reorder the protocol. Alternatively, the user could tap a block in the flowchart in order to have parameters for that block displayed, so that the user can change such parameters (e.g., ventilation volume or time between ventilations). Data describing such an edited protocol may then be saved with other information about an incident so that later users may review it, and a user may save reordered protocols so that they can be employed more easily and quickly in the future.

In this manner, the system 100 permits various portable electronic devices to communicate with each other so as to coordinate care that is provided to a victim 102. Each such device may sense information about the care provided to the victim 102, and/or may provide instructions or may store data about such care. As a result, the system 100 may provide improved care for the victim 102 by better integrating and coordinating each form of the care that the victim 102 receives. The victim 102 made thus receive improved care and an improved chance of obtaining a positive outcome from an event.

In certain instances, a condition of a victim that is used to generate a protocol for treatment of the victim may be based on on-site observations made by a rescuer, by information in an EMR for the victim, or both. For example, a determination from an EMR that a victim is taking a particular drug may result in a change in protocol for ventilation rate.

Likewise, an observation by a rescuer that the victim has suffered a head injury on site may also affect the protocol for ventilation rate. The two factors may also be considered together to determine yet a more refined ventilation rate for which a rescuer will be instructed to provide to the victim.

Thus, in operation, a two-person rescue team may arrive at a scene. One member of the team may set up and attach a defibrillator, and do the same with a ventilation bag assembly. The other member may begin an examination of the victim and enter information obtained from the examination into a portable computing device such as a general tablet computer (e.g., an iPad or netbook). In some situations, the second rescuer may be able to verbally interview the victim, at least initially, so as to determine whether the victim is lucid, what drugs the victim may be taking, and the like. The second rescuer could also make visual observations (e.g., types of trauma to the victim) and record those in the computing device. Moreover, one of the rescuers may obtain vital sign information for the victim, and such information may be entered manually into the computing device or automatically, such as through wireless links from a blood pressure cuff, or other relevant medical device.

The computing device, using all of the entered information, may then generate a protocol for treating the victim. Such a generating may occur by selecting from among a plurality of available protocols by plugging the observations into a protocol selector. The generation may also be more dynamic, and may depends on a series of heuristics that use the observations as inputs, and generate a protocol (which may be made up of one or more sub-protocols) as an output. Moreover, a lookup table may be consulted, where the table may define correlations between particular observed patient conditions or physical parameters, and a particular feature of a treatment protocol.

The computing device may also submit the observation information over a network such as the internet, and a protocol may be generated by a central computer server system and then automatically downloaded to, and implemented by, the portable computing device. Such an approach may have the benefit of being able to easily update and modify protocol-generation rules.

The computing device may then receive information about the performance by the rescuers, such as from wired or wireless transmitters on a defibrillator, an assisted ventilation unit, or other medical device (e.g., blood pressure reader). The computing device may provide feedback or coaching when the performance falls out of line with a defined protocol, or may provide feedback to maintain the performance in line with the protocol. Also, the computing device may update the protocol as care is being provided to the victim. For example, the rate of required ventilation or chest compressions may change as a function of time. Also, if one of the rescuers attaches an oxygen source to a ventilation assembly (as sensed, e.g., by a switch where the connection occurs, by a manual rescuer input to the system, or by sensors in the assisted ventilation system), the rate of required ventilation may change. Other changes in the patient condition, such as changes in measured levels of $ETCO_2$ or $SpO_2$, can lead to the computing device generating a revised protocol and providing feedback to the rescuers so that they adapt to the revised protocol (sometimes without consciously knowing that the protocol has been revised).

Figure 2:
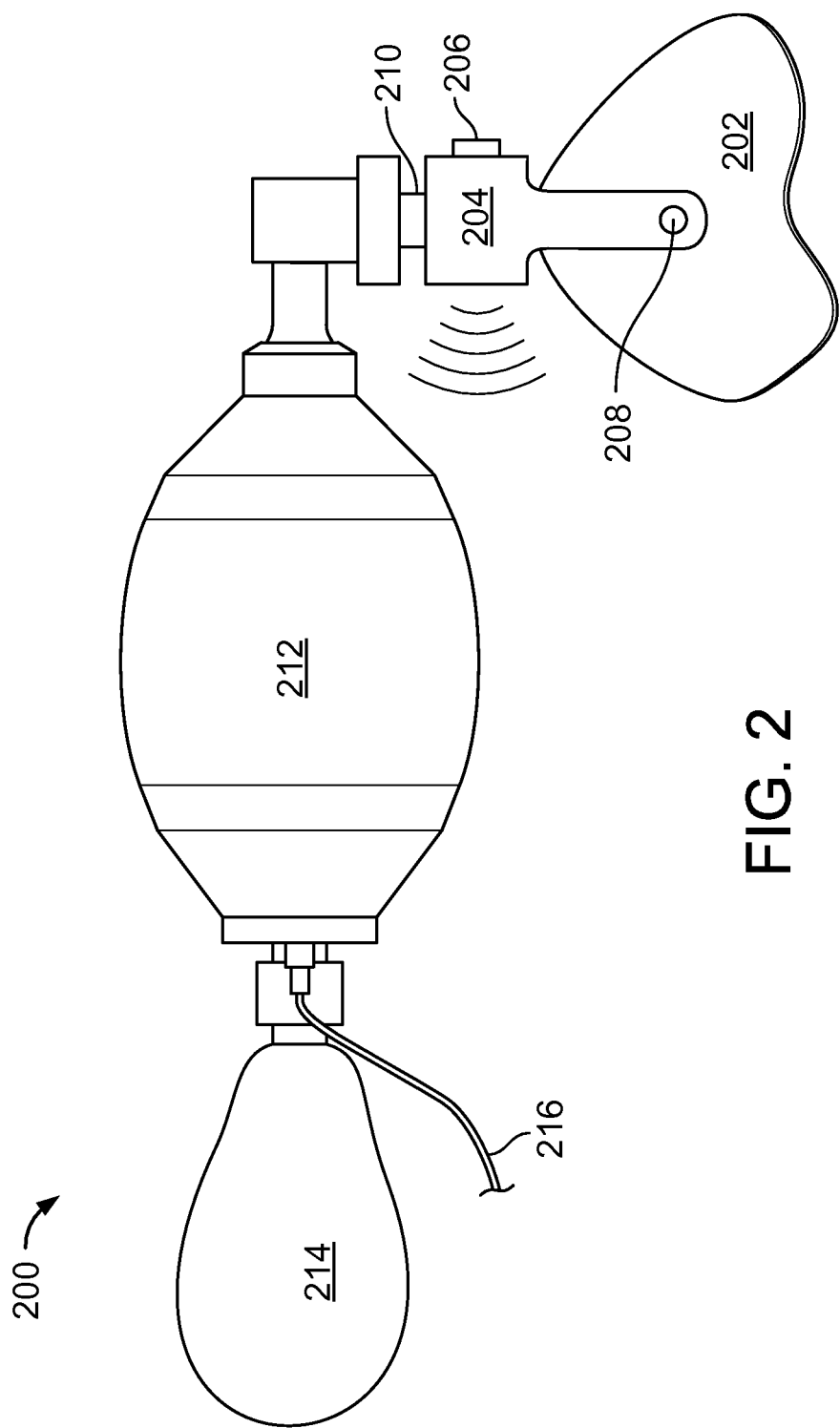
FIG. 2 shows an example of an airflow sensor.

FIG. 2 shows an example of an airflow sensor 204 used with a ventilation bag assembly 200, which may be used to ventilate a patient or victim of an accident. In this example, the airflow sensor 204 is mounted as an integral part of the ventilation bag assembly 200. The assembly 200 includes a face mask 202 which is formed from a flexible material that is configured to produce a tight seal around the periphery of a victim's mouth so that air provided by the assembly 200 may be forced into the victim's airway, and thus the victim may be properly ventilated.

The force for ventilating the patient is provided by compression of a ventilation bag body 212, which itself may be made of a flexible material that is sized and shaped so that the rescuer may place his or her hands around the body 212 and squeeze to force ventilation air into a victim. A reservoir attached to the body 212 may serve as an area for mixing of gases to be introduced, in a familiar manner. An oxygen supply line 216 is also provided and connected to the body 212, so that supplemental oxygen may be conveniently provided to a victim by way of the ventilation bag assembly 200.

A neck 210 extends from the body 212 and forms a right angle for purposes of permitting the assembly 200 to be held in a comfortable position relative to a victim's face when the mask 202 is sealed to the face. The neck 212 is a tube having a round cross-section that defines an airflow path in its interior portion, so that air may flow out of the body 212. Through the neck 210, and into the mask 202. Attached between the neck 210 and the mask 202 is the airflow sensor 204. The airflow sensor 204 may itself define an interior passage that is matched to an exterior diameter of an extension of the neck 210 and an extension of the mask 202. As a result, the airflow sensor 204 may be friction fit over such extensions, allowing the airflow sensor 204 to be added conveniently to a system that is not designed initially to have an airflow sensor, such as airflow sensor 204.

The airflow sensor 204 may operate in various known manners to detect and measure the presence of airflow in or out of a victim, and in certain implementations, to measure a volume of airflow in or out of the victim. For example, the airflow sensor 204 may include a differential pressure sensor that is attached to a venturi mechanism in an airflow path inside sensor 204. A differential pressure sensor may also be provided in coordination with a beam that substantially bisects an airflow path inside sensor 204. Taps from the differential pressure sensor may extend from discrete sides of the beam, so that the presence and volume of airflow may be determined by the difference in pressure measured between the taps. The beam may be positioned and shaped so as to provide more accurate readings, in known manners.

The sensor 204 may include an activation button 206 that, when pressed, causes the sensor 204 to activate and to begin attempting to communicate with other medical devices in its vicinity. The sensor 204, for example, may communicate using BLUETOOTH technology and may establish a connection with another device through standard BLUETOOTH handshaking mechanisms. Once the wireless connection is made, the device 204 may determine how frequently to send updates to another medical device, and may begin sending such updates. In certain implementations, the sensor 204 may also receive input from such other devices, such as input for providing a rescuer with instruction in the performance of rescue operations.

Although shown externally in the figure for manual activation, the button 206 may be mounted internally to sensor 204, such that it is activated as soon as neck 210 is inserted into sensor 204. The button 206 may instead be represented by a magnetic switch that is automatically activated when the sensor 204 is assembled with the neck 210 or the mask 202. The sensor 204 may also be activated in other relevant manners such as by a mercury switch, motion detector, or other appropriate mechanism.

An LED light 208 is shown connected to the sensor 204 and may be used to provide feedback to a user of the sensor 204. For example, the LED light 208 may blink each time ventilation is to be provided to a victim, so as to provide visual orientation for a rescuer. In this example, the LED light 208 is shown at the end of an elongated flexible strip, so as to position the LED light 208 at a location that is more likely to be seen by a rescuer, and less likely to be blocked visually by the body 212 of ventilation bag assembly 200. The LED light 208 can also be mounted directly in the body of sensor 204 in appropriate circumstances.

In other implementations, multiple modes of feedback may be provided (e.g., both rate and volume). In such a situation, a first LED, which may backlight a letter "R" for rate, and another may backlight a letter "V" for volume, and/or a pair of LEDs may be located on opposed sides of the letter, with lighting of an LED behind the letter indicating that the rate or volume being applied by the rescuer, respectively, is correct. The LEDs to the side of the letter may be lit alternatively, depending on whether the rescuer is being prompted to increase or decrease their rate or volume of ventilation.

The assembly 200 thus enables the performance of ventilation on a victim to be monitored and feedback to be provided to a rescuer. Such feedback may be provided from a computing device that takes into account various parameters of the victim's medical history and/or current medical condition, and coordinates the activities of the various medical devices that are treating the victim at one time.

Other sensors, not shown here, may also be used with a monitoring and feedback system. For example, airway gas detectors may be used, including to determine a level of oxygen that is being provided to a patient through a mask. In addition, differential absorption characteristics of $CO_2$ in red and infrared (IR) wavelengths may also be measured. Also, trans-thoracic impedance may be measured in order to determine, for example, when problems with an intubation have occurred (e.g., the tube becomes dislodged from bouncing on stairs or in an ambulance). Checks for intubation tube status can also be linked to the airflow sensor, so that the checks are begun when ventilation of the victim begins. The various coordinated sensors may also be used, in certain instances, to move a procedure outside of a standard protocol, or to follow a protocol that has been designed to be more flexible and responsive to patient needs than are typical protocols that depend on the limited capabilities of one or two caregivers.

Also, sensors other than airflow sensors may be used to determine a ventilation rate. For example, a strain sensor may be provided on the bag of a ventilation assembly, and may be used to determine how frequently the bag is being squeezed, and by extension the rate of assisted ventilation being provided to a victim.

Figure 3:
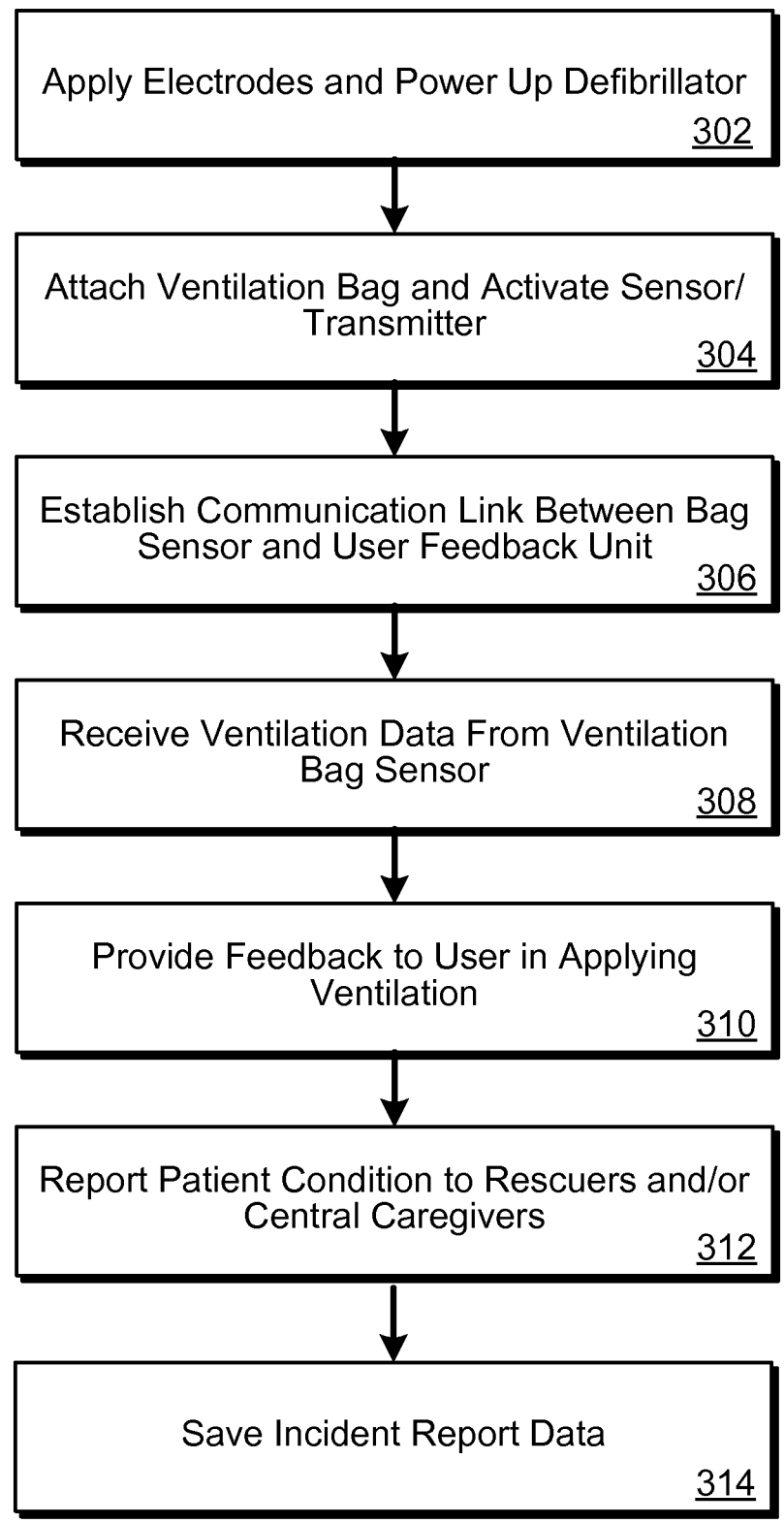
FIG. 3 is a flowchart of a process for providing feedback to a caregiver who is operating a ventilation bag or similar structure.

FIG. 3A is a flowchart of a process for providing feedback to a caregiver who is operating a ventilation bag or similar structure. In general, the process involves deploying various medical devices at the scene of an emergency and causing the devices to coordinate their operations so as to improve the care that is given to a victim at the scene.

The process begins at box 302, where electrodes for a defibrillator are applied to a victim and the defibrillator is powered up. Such action may occur soon after rescuers, who may be lay rescuers using an AED or emergency medical technicians using an advanced defibrillator, arrive on a scene and recognize that a victim is in need of defibrillation.

At box 304, a ventilation bag is attached to the victim and an airflow sensor associated with the bag is activated. In one example, a second emergency medical technician may be assigned this task and may recognize that the victim's airway is patent and is not in need of incubation at the moment, and may deploy the ventilation bag to begin providing forced ventilation to the victim.

At box 306, a communication link is established between the bag airflow sensor and a feedback unit, which may be in the form of a tablet, like tablet 116 in FIG. 1, or a defibrillator like defibrillator 112 in FIG. 1. The communication may occur automatically upon activating the two communicating components, such as by instigating an automatic BLUETOOTH or WiFi connection in a familiar manner.

At box 308, ventilation data is received from the ventilation bag airflow sensor. The ventilation data may simply include time stamped indicators of the start or end of inhalation and/or exhalation for the victim. The data may also include information about the length of inhalation or exhalation, and the volume of air moved by the victim or for the victim. Such information may be passed from the airflow sensor to a computing component such as tablet 116. The data may then be compared against a protocol for providing ventilation, and determinations may be made with respect to whether the ventilation is being properly or improperly applied relative to that protocol. Also, coordination of the ventilation with other actions being taken on the victim (e.g., chest compressions) may also be performed via a device such as tablet 116.

Upon the device making such determinations, it may provide feedback to the rescuer in applying ventilation, as shown at box 310. For example, the tablet 116 may provide visual or audible feedback to guide a rescuer regarding when and with how much force to squeeze a ventilation bag. The tablet 116 may also communicate data to another device, such as a defibrillator or back to the airflow sensor, and that receiving device may provide the feedback to the caregiver. In addition, information may be provided to a headset or other personal interface worn by the particular rescuer, which may enable feedback provided to one rescuer to be separated from feedback provided to the other rescuer, so that the rescuers are less likely to become confused with the feedback. In addition, other communications may occur through such headsets, such as communications between cooperating caregivers, and communications from a dispatch center or from a central physician such as an emergency room physician who is tracking the progress of the team of the EMTs, or providing input to such a team.

The feedback provided may follow a set protocol that does not differ from victim to victim, or may be customized for he particular victim. For example, the rate and volume of ventilation to provide a victim may depend on how long the victim has been suffering from a current condition. Thus, a rescuer may try to ascertain how long the victim has been down, or a time stamp from the time at which an emergency was called in may be used as a proxy. Also, various states of the victim may be relevant to the rate and volume of ventilation to be provided to the victim, including:

Pediatric vs. adult

Patient condition (e.g. traumatic brain injury vs. cardiac arrest)

Characteristics of the ECG may also suggest different ventilation requirements. For example, patients with ventricular fibrillation may have lower ventilation requirements than patients with asystole or PEA.

Etiology of disease—cardiac arrest due to drowning vs. presumed myocardial infarction.

Duration of patient downtime for cardiac arrest.

Presence/absence of (effective) bystander CPR (compressions and/or ventilations) prior to arrival of EMS.

ETCO2—there are recommendations to titrate ventilation rate to achieve a particular end tidal CO2 value.

SpO2—adjust ventilation rate to achieve optimal peripheral oxygen saturation.

At box 312, the system reports the victim's condition to rescuers and may also report the condition of the victim to central caregivers, such as physicians or other staff in an emergency room where the victim will be taken. Such reporting may include providing ECG readout information, vital signs, and other relevant information needed by the immediate (e.g., EMT's) or secondary (e.g., ER Physicians) caregivers.

At box 314, incident report data is saved, such as by sending the data from one or more of the portable medical devices at a scene to a central electronic medical record system. The data may be gathered initially at one device such as tablet 116, and may then be forwarded to the central system. The incident report data may include information regarding drugs and other treatments provided to the patient, and other information that may be relevant to downstream caregivers, such as emergency room physicians.

In this manner, and using this example process, information relating to various aspects of care given to a victim at the scene of an accident may be collected, and treatment of the patient may be coordinated, including by coordinating the provision of chest compressions, defibrillation shocks, and ventilation to the patient.

Figure 4:
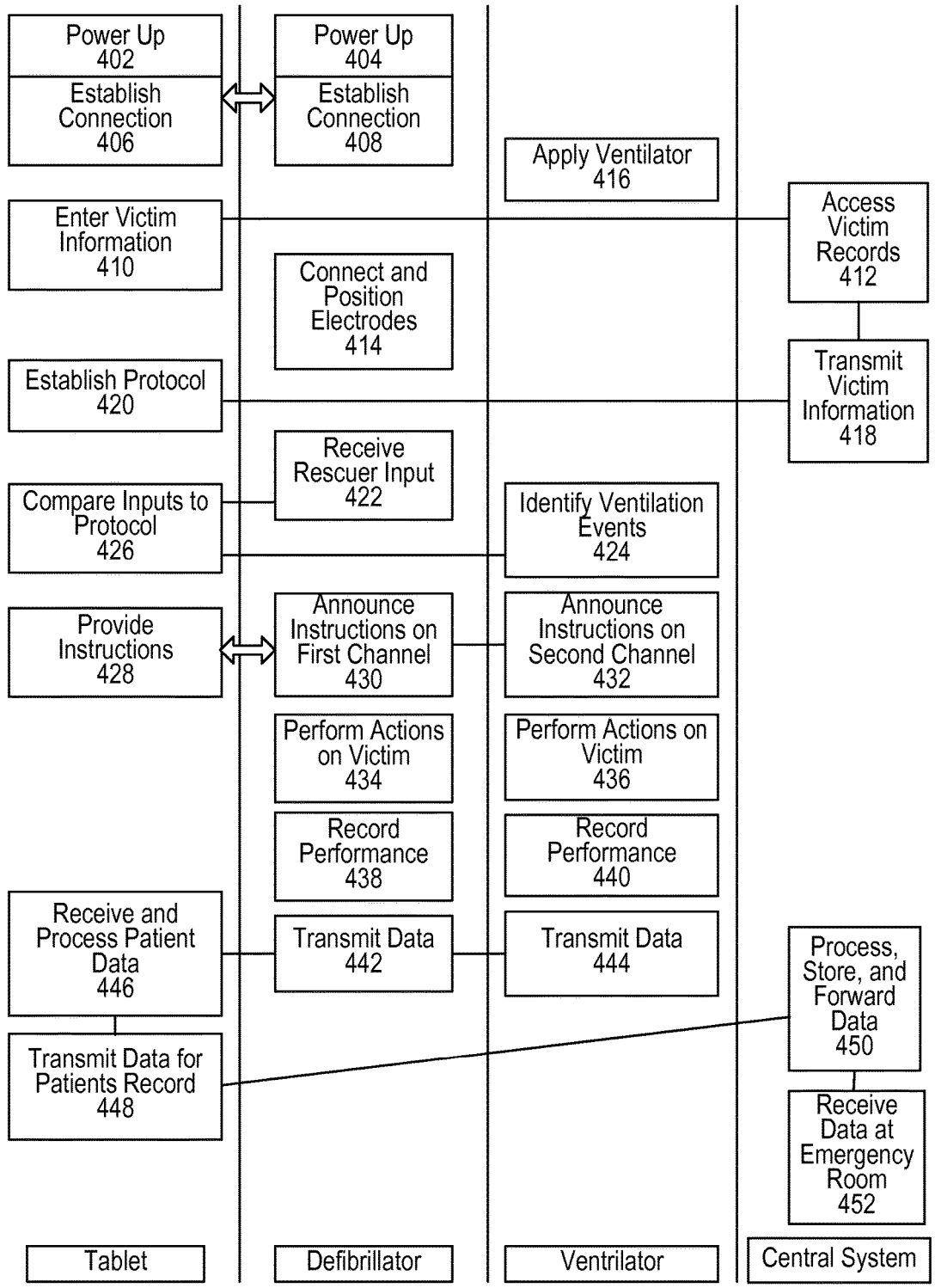
FIG. 4 is a swim lane diagram of a process by which various parameters can be used to provide feedback to one or more medical rescuers.

FIG. 4A is a swim lane diagram of a process by which various parameters can be used to provide feedback to one or more medical rescuers. In general, the process is similar to that shown in FIG. 3A, though particular example structures are shown in this figure as performing certain steps in the process. The particular steps that are carried out by each structure or device can be changed as is appropriate, and other steps may be added, steps may be rearranged or modified, or steps may be removed from the process.

The process begins at boxes 402 and 404, where a tablet and defibrillator are powered up at the site of an emergency. Such powering may simply involve deploying them from emergency vehicles and activating power switches on each such device. At boxes 406 and 408, a wireless communication connection is established between the tablet and the defibrillator for the transfer of data between the two devices while care is being provided to a victim at the emergency scene.

At box 410, victim information is entered into the tablet (though at least some of the information may also have been previously entered by a dispatcher, and that information may auto-populate on the device). Such information may include a name or alphanumeric ID number of the victim, as a mechanism for retrieving electronic medical record information about the victim. Such information may also include information about the current condition of the victim. For example, a caregiver may record whether the victim has suffered head trauma, whether the victim is bleeding, has broken bones, approximately age and gender of the victim, and other information that may be relative to the care to be given to the victim. Such information may be entered on a touchscreen display, including by selecting input values from a menuing system (including a system that performs a question-and-answer interview session with a rescuer), or could also be provided by a spoken input to the tablet.

Where an identifier for a victim, such as a name of the victim is provided, the tablet may attempt to access records in a central system, as shown by box 412. Where the tablet has provided appropriate credentials, such as identifier and password of an emergency medical technician, the central system may transmit medical record information about the victim, at box 418, back to the tablet. Upon receiving additional information about the victim, the tablet may establish a protocol for treatment of the victim, and may begin carrying out the protocol by instructing rescuers at the scene. For example, the condition of the victim, the victim's age, the victim's medical history, and the victim's size, may all be relevant to the manner in which chest compressions, defibrillation shocks, and ventilation are provided to the victim. The protocol established by the tablet may take into account each relevant factor in developing a plan of treatment.

While the system is obtaining data and developing a plan, a caregiver at the site may be connecting and positioning electrodes on the victim's chest (box 414), and the same caregiver or another caregiver may be applying a ventilator (box 416) on the victim.

The caregivers may then begin executing the protocol, such as by applying chest compressions and ventilation to the victim. At boxes 422 and 424, the defibrillator provides received rescue data to the tablet, such as by transmitting information regarding the victim's ECG and also the manner in which chest compressions have been applied to the victim, and the ventilator or ventilation sensor may provide information about ventilator events. Such information may include, for example, the frequency with which ventilation is being applied, and also the volume of ventilation air being provided.

At box 426, the tablet compares the received inputs to the appropriate protocol, which may be a static protocol or may be a dynamic protocol that changes as treatment of the victim continues. Where the inputs do not match the protocol so that corrective action by the caregivers is required, the tablet may provide instructions (box 428) to the caregivers. For example, the tablet may transmit information to the defibrillator, and the defibrillator may be caused to announce instructions to a provider of chess compressions, such as having a speaker on the defibrillator state those instructions (box 430). The tablet may also send data to the ventilator, causing the ventilator to announce instructions to another caregiver (box 432), either visually or audibly.

At boxes 434 and 436, respectively, the caregiver providing chest compressions and operating the defibrillator may follow the received instructions, and a caregiver operating the ventilating device may follow the other appropriate instructions. At boxes 438 and 440, respectively, the defibrillator and the ventilator may record the performance of the particular caregiver in response to the instructions. Such performance data may be stored and transmitted back to the tablet at boxes 442 and 444. The data may indicate whether the relevant caregivers have altered their actions sufficiently to place their activities back within the protocol ranges. Also, the protocol may change over time, such as by calling for a certain period of chess compressions followed by the provision of electric shock to the patient for defibrillation. Thus, the tablet, at box 428 may change the instructions that it provides so as to match the changes in the protocol.

At box 446, the tablet receives and processes the patient data. The process may then loop back to box 428 and until treatment of the victim is completed. Changes may be made to the protocol as treatment continues also, such as by recognizing that the patient has been without a normal heart rhythm for particular time, and adjusting the timing and sequencing of care given to the victim based on such a determination.

At box 448, data is transmitted for the patient's record to the central system. Such data may be provided consistently throughout provision of care, such as by providing ECG and vital signs data that may be reviewed in real time by a central emergency room physician who accesses the central system. The data may also be provided when the care is complete, such as may be recognized by the powering down of the tablet, defibrillator, or ventilator, so that the medical devices may be returned to an ambulance or other vehicle in which the patient is transported to an emergency room. Also, the tablet may invoke additional dialogue with one of the caregivers on such a trip, so as to complete the patient record before the caregivers move to another project.

At box 450, the central system processes, stores, and forwards, relevant data regarding the victim. For example, the treatment information, such as drugs that may have been given to the patient through intravenous tubes, may be recorded and added to the victim's medical record. In addition, a billing system may be notified, and appropriate fees may be applied to a victim's account in such a system. Moreover, a snapshot of relevant data from the treatment may be provided in advance to an emergency room team at a hospital where the patient has been taken. Then, at box 452, the relevant data is received at the emergency room, so that the emergency room team can review it when providing further treatment for the patient.

Figure 5:
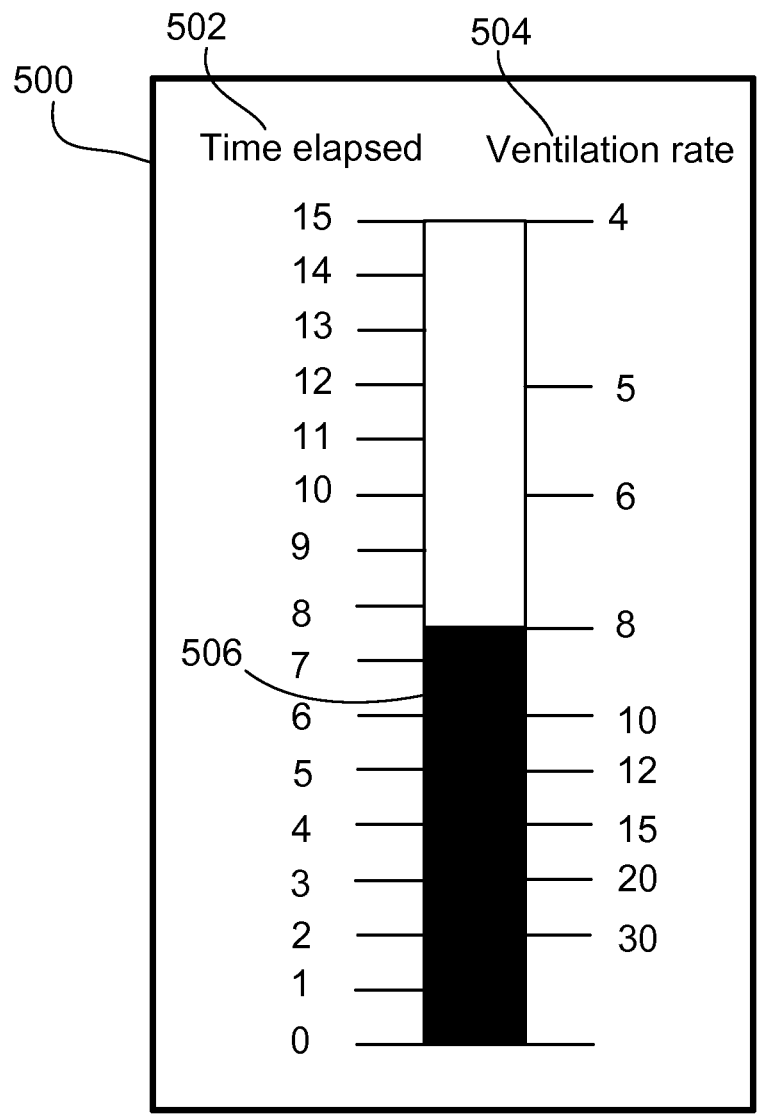
FIGS. 5 and 6 show an example of a visual feedback provided to a caregiver.

FIG. 5 shows exemplary information, e.g., a ventilation timer 500, displayed on a display device to a rescuer during the administration of ventilation to a patient. The ventilation timer 500 provides information to the rescuer to help the rescuer control the rate of ventilation provided to the patient. The ventilation timer 500 can include a bar 506 (or other shape) that that fills as time elapses between breaths. The bar 506 can include scaling information (e.g., tick marks on the graph) that provide information about the elapsed time 502 and/or ventilation rate 504. The elapsed time 502 provides an indication of the amount of time that has passed since the last ventilation event and the respiration rate 504 provides the number of breaths per minute (e.g., 5 seconds between breaths=12 breaths/minute).

The information displayed on the ventilation timer 500 is based on ventilation related data received from a device that detects when a ventilation has been delivered (e.g., a flow meter, capnography, thoracic impedance). The ventilation related information is used by a computer to provide an input indicating when to re-start the timer such that the elapsed time can be determined.

In some examples, the information presented on the ventilation timer 500 can be color coded or otherwise supplemented by a visual indicator of ranges that indicate adequate ventilation versus sub-optimal ventilation. In one example, the color of the bar 506 in the ventilation timer can change based on the adequacy of the ventilation. For example, the bar could be colored green when proper ventilation is being provided and yellow or red when the ventilation falls outside the desired range of respiration rates. Additionally, in some examples, an indication of whether the user should increase or decrease the rate of respiration could be provided. Additionally, in some examples, an indication of the optimal elapsed time/ventilation rate could be provided such as by overlaying a line or other indicator at the desired level so the rescuer can attempt to have the bar 506 match the displayed optimal timing indicator.

In some additional examples, the information presented in the ventilation timer 500 can be color coded or otherwise supplemented by other visual indicator based on the nature of the underlying condition being treated, e.g. respiratory distress vs cardiac arrest vs TBI. Additionally, the range that is indicated as an optimal or an acceptable respiration rate can change based on information from one or more physiologic monitoring sensors and estimate from those sensor(s) of the underlying status of the patient's cardiopulmonary status. Such physiologic monitoring can be based, for example on information about $EtCO_2$ (e.g., the partial pressure or maximal concentration of carbon dioxide, $CO_2$ at the end of an exhaled breath, which is expressed as a percentage of $CO_2$ or mmHg) and/or information about oxygen saturation from a pulse oximeter, a medical device that indirectly monitors the oxygen saturation of a patient's blood. Such physiologic monitoring can also include information from a tissue $CO_2$ sensor that can be used to calculate the blood oxygen concentration, for example, based on the ventilation/perfusion ratio (or V/Q ratio) which provides a measurement used to assess the efficiency and adequacy of the matching of the amount air reaching the alevoli to the amount of blood reaching the alveoli (sometimes reported as the VQ mismatch which is used to express when the ventilation and the perfusion of a gas exchanging unit are not matched).

Figure 6:
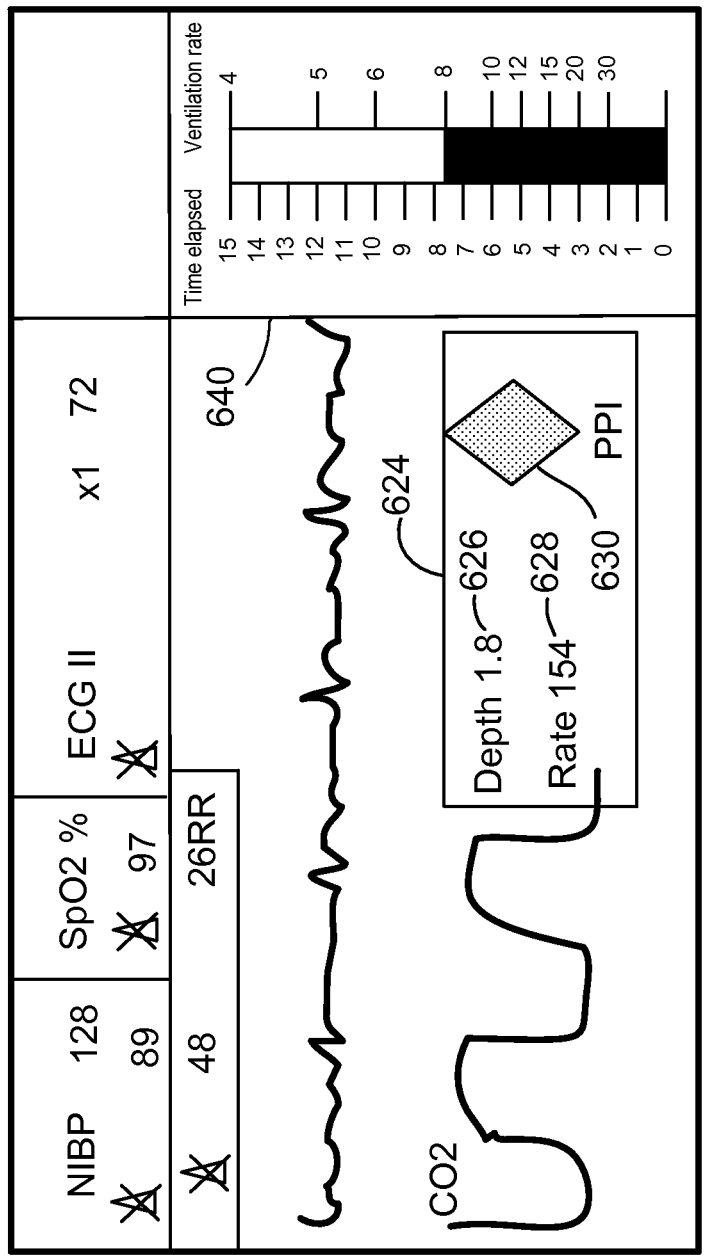

FIG. 6 shows exemplary information displayed during the administration of ventilation and CPR compressions to a patient. The system automatically switches the information presented based on whether chest compressions are detected and whether appropriate ventilation is detected. For example, CO2 or depth of chest compressions may be displayed (e.g., a CO2 waveform 620 is displayed in FIG. 8B) during CPR administration and upon detection of the cessation of chest compressions the waveform can be switched to display and SpO2 or pulse waveform (not shown).

A portion 640 of the display can include ventilation information such as a ventilation timer (e.g., as described above in relation to FIG. 5) providing information about respiratory rate associated with the elapsed time between ventilations.

Another portion 624 of the display can include information about the CPR such as depth 626, rate 628 and perfusion performance indicator (PPI) 630. 520. The PPI 630 is a shape (e.g., a diamond) with the amount of fill in the shape differing to provide feedback about both the rate and depth of the compressions. When CPR is being performed adequately, for example, at a rate of about 100 compressions/minute (CPM) with the depth of each compression greater than 1.5 inches, the entire indicator will be filled. As the rate and/or depth decreases below acceptable limits, the amount of fill lessens. The PPI 520 provides a visual indication of the quality of the CPR such that the rescuer can aim to keep the PPI 520 completely filled.

Figure 7:
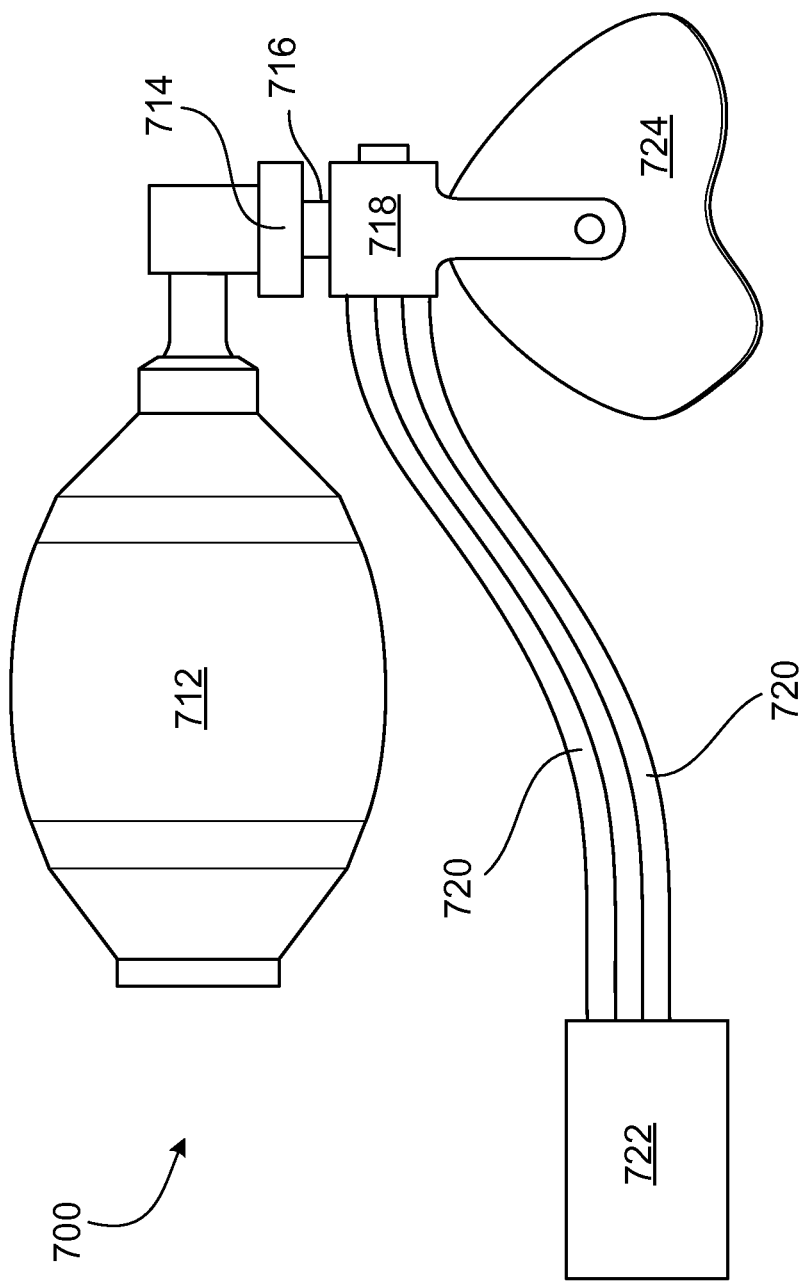
FIG. 7 shows an example of a ventilation assembly.

FIG. 7 shows an example of a ventilation assembly 700 for providing manual ventilation to a victim. The ventilation assembly 700 is designed to be sealed around the mouth of a victim (e.g., as shown in FIG. 1). The ventilation assembly 700 may include a flexible body structure 712 that a rescuer may squeeze periodically to provide ventilation on the victim when the victim is not breathing sufficiently on his or her own. More particularly, the ventilation assembly 700 includes a face mask 724 which is formed from a flexible material that is configured to produce a tight seal around the periphery of a victim's mouth so that air provided by the ventilation assembly 700 may be forced into the victim's airway by squeezing the flexible body structure 712, and thus the victim may be properly ventilated.

Provided with the ventilation assembly 700 is an airflow sensor 718. The airflow sensor 718 is located in a neck of the ventilation assembly 700 near the mouthpiece or mask 724 of the ventilation bag. The airflow sensor 718 monitors the flow of air into and out of the patient's mouth, to identify a rate at which ventilation is occurring with the victim. In addition, the airflow sensor 718 monitors a volume of airflow into and out of the victim. For example, the airflow sensor 718 may include a differential pressure sensor that is attached to a venturi mechanism in an airflow path inside sensor 204.

The ventilation assembly 700 also includes a capnometer 714 or other carbon-dioxide measurement device. The capnometer 714 is an infra-red spectrograph for monitoring $CO_2$. Carbon dioxide selectively absorbs specific wavelengths of IR light. Since the amount of light absorbed is proportional to the concentration of the absorbing molecules, the concentration of a gas can be determined by comparing the measured absorbance with the absorbance of a known standard. The $CO_2$ concentration measured by the monitor can be expressed as partial pressure in mmHg or percentage $CO_2$ ($FCO_2$).

The airflow sensor may also include sensors for measuring gas concentration, such as carbon dioxide ($CO_2$), nitrogen and oxygen. Exemplary $CO_2$ concentration sensors include those provided in commercial capnographs that measure infrared light absorption known to those skilled in the art. Oxygen gas partial pressure may be measured by so-called a $ppO_2$ meter such as is used in SCUBA-diving, in re-breathing apparatus. A specific example is the PSR-11-33-NMI oxygen sensor manufactured by Analytic Industries, Inc. (Pomona Calif.). This sensor works off the principle of an electro-galvanic fuel cell. Oxygen concentration sensing may also be done with an oxygen optode. In general, an oxygen optode is a sensor based on optical measurement of the oxygen concentration. In some examples of oxygen optodes, a chemical film is glued to the tip of an optical cable and the fluorescence properties of this film depend on the oxygen concentration. Fluorescence is at a maximum when there is no oxygen present. When an $O_2$ molecule is present and collides with the film, this quenches the photoluminescence. For a given oxygen concentration there will be a specific number of $O_2$ molecules colliding with the film at any given time, and the fluorescence properties will be stable. Thus, by observing the fluorescence properties $O_2$ concentration can be determined.

The total volume of the ventilation gas delivered to and from the lungs is calculated by measuring the continuous flow rate for each individual inhalation and exhalation and then integrating the flow over time to compute volume. Because concentrations are available for each of the measured gases is known for each instant, the volumes delivered for each ventilation for each of the specific gases is also calculated along with the volume delivered for all other gases not measured. In one embodiment, the measured gases are $CO_2$ and oxygen, with the remaining gases being predominantly nitrogen. In other embodiments, gas concentrations for other gases may be provided such as additive gases that have therapeutic value such as anaesthetic gases, nitric oxide or a noble gas such as Argon.

In addition, the so-called minute-volume, known to those skilled in the art, for each of the measured constituent gases can be calculated. In general, minute-volume is the quantity of gas delivered to the patient, or exhaled from the patient in the case of $CO_2$, over a one-minute period. Unlike tidal volume which is the volume delivered for a particular breath, minute volume is based on the one-minute period. The calculated minute-volume for any point in time may be calculated by summing each of the individual tidal volumes in the previous minute, or it may be estimated based on the tidal volumes of breaths occurring within some predefined time period in the immediate past.

The ventilation assembly 700 also includes a pressure sensor 722. The pressure sensor 720 may be located on the electrode pad assembly. Tubing 720 is connected between the electrode assembly and an adapter positioned in the airway. If a differential pressure measurement is being made, two tubes 720 are brought from the adapter to the electrode assembly. The adapter has a small vane positioned between the pressure sensing ports so that the pressure difference generated between the two ports is proportional to the velocity of air flow through the adapter into the patient. Knowing the cross-sectional area of the air path through the adapter, allows the tidal volume to be estimated (using known differential pressure tidal volume measurement techniques).

Other sensors may also be used with a monitoring and feedback system. For example, additional airway gas detectors may be used, including a detector to determine a level of oxygen that is being provided to a patient through a mask. Also, trans-thoracic impedance may be measured in order to determine, for example, when problems with an intubation have occurred (e.g., the tube becomes dislodged).

The ventilation assembly 700 thus enables the performance of ventilation on a victim to be monitored and feedback to be provided to a rescuer. Such feedback may be provided from a computing device that takes into account various parameters of the victim's medical history and/or current medical condition, and coordinates the activities of the various medical devices that are treating the victim at one time. For example, the sensors described above can be joined with a computer, tablet, or other processing device by a wired connection or by a short-range wireless data transmitter or transceiver, such as a mechanism communicating via BLUETOOTH technology. Based on the received information, the device can provide feedback about the ventilation to the rescuer, for example, by telling a rescuer to squeeze the ventilation bag 712 harder or softer, or faster or slower.

Figure 8A:
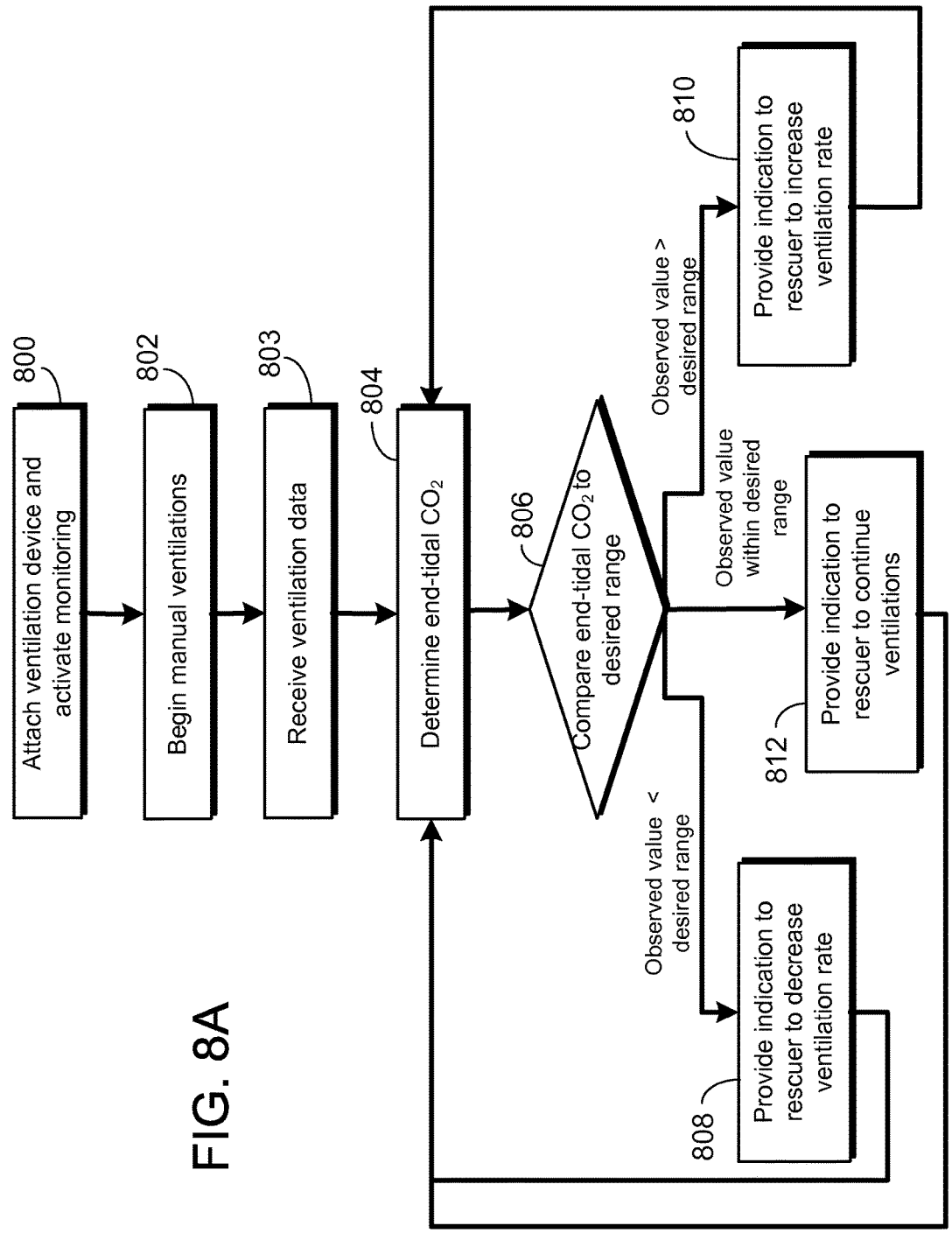
FIG. 8A is a flowchart of a process for providing feedback to a caregiver who is operating a ventilation bag or similar structure.

FIG. 8A is a flowchart of a process for providing feedback to a caregiver who is operating the ventilation bag 712. In general, the process involves deploying various medical devices including a ventilation device at the scene of an emergency and providing feedback to the rescuer in relation to ventilation of a victim.

The process begins at box 800, where the rescuer attaches a ventilation bag to the victim and various sensors associated with the bag are activated. A communication link is also established between the sensors and a feedback unit, which may be in the form of a tablet, like tablet 116 in FIG. 1, or a defibrillator like defibrillator 112 in FIG. 1. The communication may occur automatically upon activating the two communicating components, such as by instigating an automatic BLUETOOTH or WiFi connection in a familiar manner.

At box 802, the rescuer begins manual ventilations. Such action may occur soon after rescuers, who may be lay rescuers using an AED or emergency medical technicians using an advanced defibrillator, arrive on a scene and recognize that a victim is in need of ventilation.

At box 803, ventilation data is received from the ventilation device. The ventilation data may include time stamped indicators of the start or end of inhalation and/or exhalation for the victim. The data may also include information about the length of inhalation or exhalation, and the volume of air moved by the victim or for the victim, and the carbon-dioxide content included in the air. Such information may be passed from the sensors to a computing component.

Figure 8B:
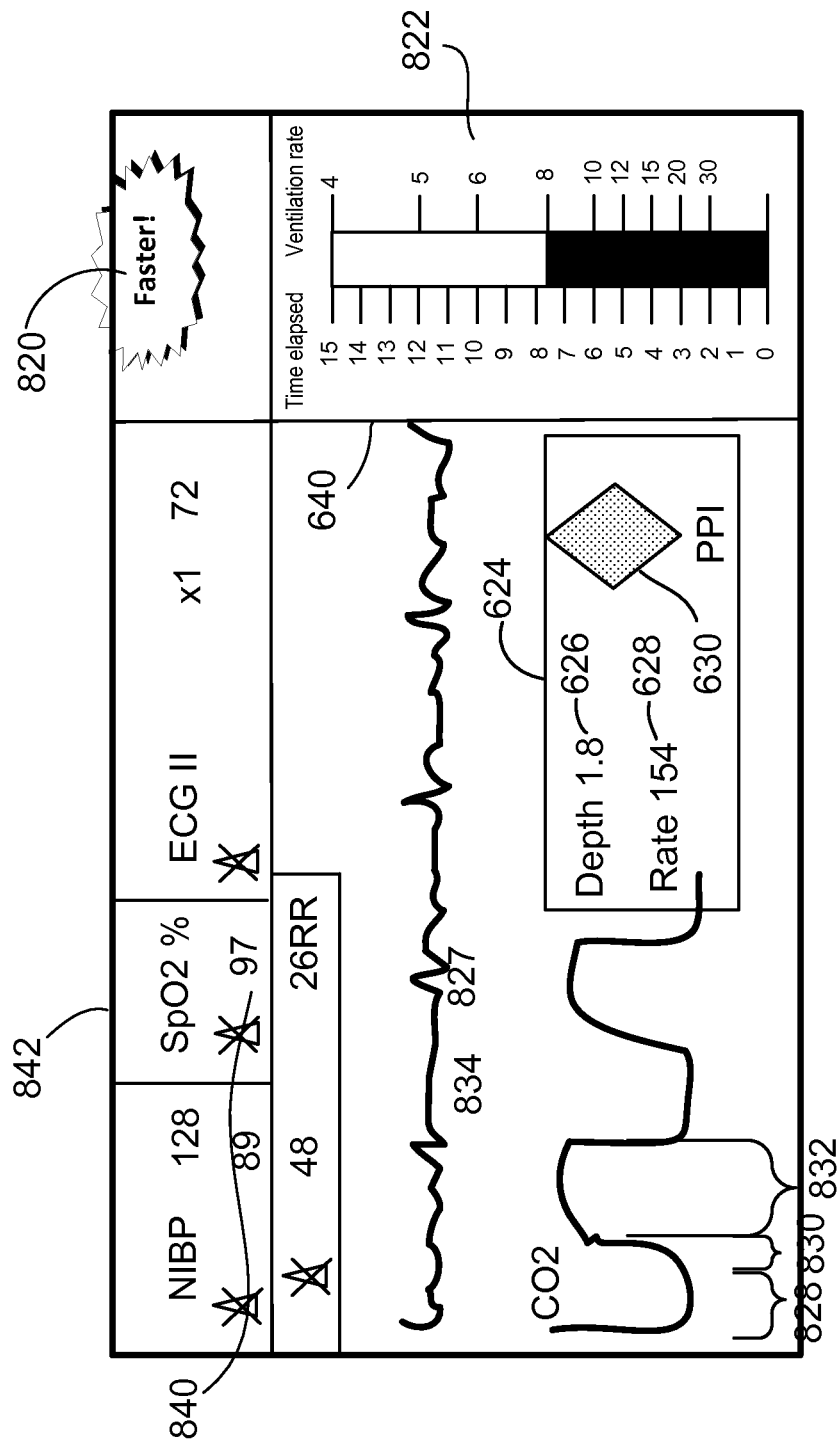
FIG. 8B shows an example of a visual feedback provided to a caregiver.

At box 804, the ventilation data is used to calculate an end-tidal $CO_2$ ($ETCO_2$). The end-tidal $CO_2$ provides an indication of the level of carbon dioxide in the air exhaled from the body at the end of a respiratory cycle, exemplary normal values of which are 4% to 6% or 35 to 45 mm Hg. $ETCO_2$ values that are less than 35 mmHg can indicate hyperventilation/hypocapnia while $ETCO_2$ values that are greater than 45 mmHg can indicate hypoventilation/hypercapnia. As shown in FIG. 8B, the measured $CO_2$ (as shown in reading 827) in a victim will vary during the respiratory cycle. Portion 828 is post inspiration/dead space exhalation. When the subject exhales, the first gas that is exhaled comes from the trachea and major bronchi which do not allow gas exchange and therefore will have a gas composition similar to the inhaled gas. Portion 830 is the start of alveolar exhalation. Portion 832 is the exhalation upstroke where dead space gas mixes with lung gas. Finally, portion 834 is the continuation of exhalation, or the plateau (all the gas is alveolar now). The end-tidal value is measured at the end of the exhillation at point 834. The gas at the end of this exhalation is considered to have come from the alveoli and reflects the equilibrium $CO_2$ concentration between the capillaries and the alveoli; the $PCO_2$ in this gas is called end-tidal $PCO_2$ ($PetCO_2$).

At box 806, the end-tidal or minute-volume $CO_2$ data is compared against a protocol for providing ventilation, and determinations are made with respect to whether the ventilation is being properly or improperly being applied relative to that protocol. For example, a range of values considered as providing proper ventilation can be used to determine whether the victim is being appropriately ventilated, over ventilated, or under ventilated. In one particular example, for conscious patients, end-tidal $CO_2$ values between 32 to 38 mm Hg can indicate proper ventilation while, end-tidal $CO_2$ that are less than 30 mmHg can indicate hyperventilation (e.g., over ventilation), and end-tidal $CO_2$ values that are greater than approximately 40 mmHg can indicate hypoventilation (e.g., under ventilation).

Minute-volume $CO_2$ measures are believed to be important during ventilation because end-tidal $CO_2$ measures are dependent on the actual volume of gas delivered to the patient. The physiologic measure that the clinician is titrating to is the amount of $CO_2$ gas exhaled from the patient, which is a good overall measure of the patient's physiologic state. Increasing the ventilation rate or tidal volume will cause $EtCO_2$ values to decrease for a fixed $CO_2$ gas elimination rate from a patient; this is not the case for minute-volume $CO_2$ measures. Thus, minute-volume measures of $CO_2$ are an important parameter in situations where ventilation is being delivered in a manual fashion with a rescuer squeezing a ventilation bag where both ventilation rates and tidal volumes have been shown in multiple studies to be completely uncontrolled in the clinical environment.

Figure 9A:
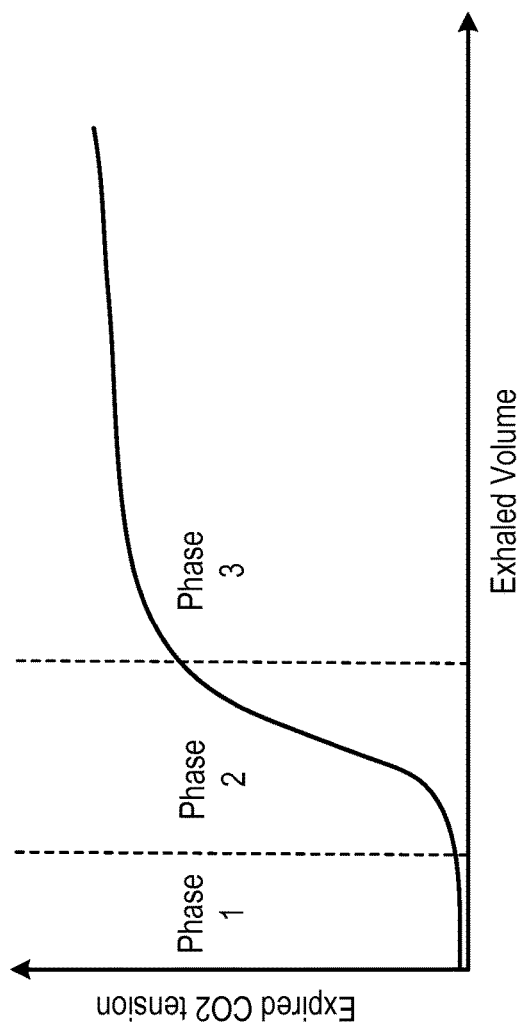
FIG. 9A and FIG. 9B show graphs of expired $CO_2$ tension versus exhaled volume.
Figure 9B:
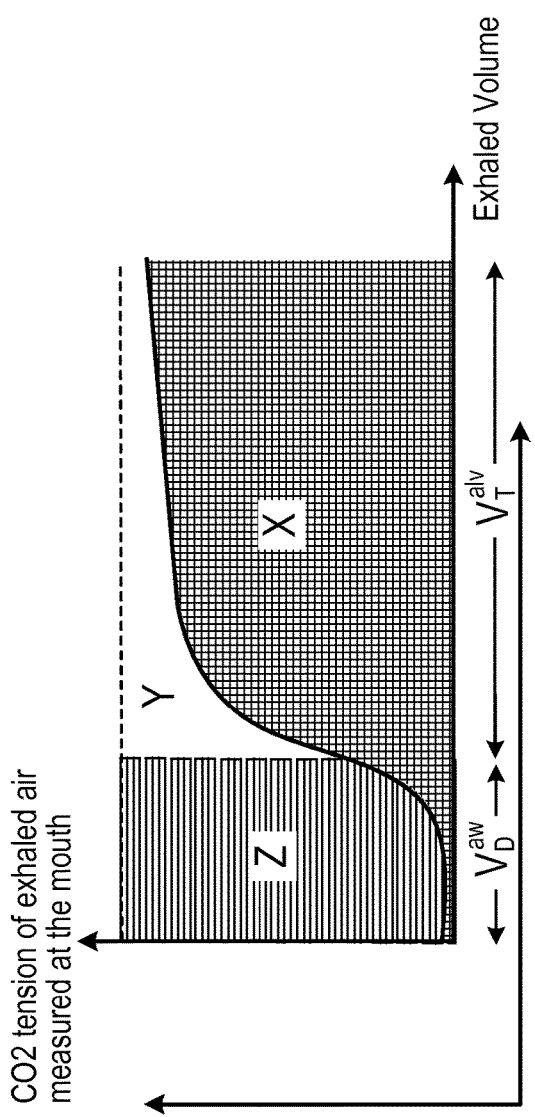

$CO_2$ concentration as a function of expired volume may be plotted such as in the form of a single-breath $CO_2$ analysis ($SBCO_2$), known to those skilled in the art. The $SBCO_2$ curve has three phases: phase 1 made up of non-alveolar gas, or ventilatory dead-space gas, that is essentially free of $CO_2$; phase 2 that is a transition phase with a characteristic S-shape that contains some amount $CO_2$; and phase 3 that is the alveolar gas bearing the predominant quantity of exhaled $CO_2$. Because the x-axis of the $SBCO_2$, or expirogram as it is sometimes called, has units of volume, calculations can be made to determine both alveolar as well as non-alveolar deadspace based on techniques known to those skilled in the art. For example, FIGS. 9A and 9B (from IEEE TRANSACTIONS ON INFORMATION TECHNOLOGY IN BIOMEDICINE, VOL. 6, NO. 4, DECEMBER 2002), each show the expired $CO_2$ tension versus exhaled volume. The non-alveolar deadspace is the area of 'Z' in FIG. 9B, and the alveolar deadspace is the area of 'Y'. The sum of these two deadspaces does not produce any gas exchange in the patient, so this sets the minimum ventilation volume for each patient. Additionally, including dynamic lung compliance in the calculation of overall lung volume using $SBCO_2$ curves may enhance the accuracy produced by $SBCO_2$-based calculations.

Referring back to FIG. 8A, upon the computing device making such determinations with respect to whether the ventilation is being properly or improperly being applied relative to that protocol (box 806), the computing device provides feedback to the rescuer applying the ventilation, as shown at boxes 808, 810, and 812. For example, the feedback can be visual or audible feedback to guide the rescuer regarding when and with how much force to squeeze a ventilation bag 712. More particularly, if the comparison of the minute-volume or end-tidal $CO_2$ to the protocol indicated that the observed minute-volume or end-tidal $CO_2$ was less than the desired range, at box 808 the rescuer can be advised to decrease ventilation (e.g., to decrease the ventilation rate by squeezing the bag less frequently or ventilation volume by squeezing the bag to a lesser extent). If the comparison of the minute-volume or end-tidal $CO_2$ to the protocol indicated that the observed end-tidal $CO_2$ was within the desired range, at box 810 the rescuer can be advised to continue ventilation. If the comparison of the minute-volume or end-tidal $CO_2$ to the protocol indicated that the observed minute-volume or end-tidal $CO_2$ was greater than the desired range, at box 812 the rescuer can be advised to increase ventilation (e.g., to increase the ventilation rate by squeezing the bag more frequently or increase ventilation volume by squeezing the bag to a greater extent). In some embodiments, during CPR, the computing device will prompt the rescuer to a ventilation rate of 10 ventilations per minute with a minute volume of 6000 ml.

In some additional embodiments, the minute-volume or end-tidal $CO_2$ can be used to provide feedback on the effectiveness of CPR compressions. Based on the minute-volume or end-tidal $CO_2$ information related to the depth of compressions can be calculated and the system can provide feedback to a rescuer to increase or decrease the depth of the CPR compressions.

For example, in a typical patient, expired $CO_2$ minute volume in a healthy patient is approximately 800-900 ml, or 14% of a typical minute volume of 6 liters. It is also know that CPR does not achieve normal perfusion in patients undergoing cardiac arrest, and expected blood flows are on the order of only 10-20% of normal flow. Therefore, a goal-directed approach is taken using volumetric expired minute-volume $CO_2$ (VEMV-$CO_2$) during compressions. During the first minute of compressions, a target of 100 ml VEMV-$CO_2$ is set and is shown on the computing device display. Compression depth is shown in real time on the display for each compression. If the depth is less than 2 inches, or other established guideline that is either the result of a standards or guidelines group like the American Heart Association, or is the result of a particular physician's guidance in the local medical system, then the computed device prompts the rescuer to compress deeper. If the compression depth is at least the minimum guideline depth, but the VEMV-$CO_2$ target has not been achieved, then the rescuer is prompted to increase the compression depth by a preset amount of, for example, 0.25 inches to 2.25 inches. If after approximately 30 seconds of compressions at the prescribed depth the VEMV-$CO_2$ is still not at least at the target, then the rescuer is prompted to increase their compression depth to 2.5 inches. The same cycle is repeated to increase compression depth to a maximum of 3 inches. If there was no change in VEMV$CO_2$ as a result of compression depth increases or is less than expected, and the rescuer is delivering ventilations at the target rate and minute volume, then the rescuer is prompted to slow down ventilation rate, for example, to 8 ventilations per minute. While in the example above, the rescuer was prompted to increase the compression depth by 0.25 inches other increases in depths (e.g., 0.1 inches, 0.3 inches, 0.5 inches) could be used.

If after 30 seconds, or some predetermined period of time to allow for the cardiopulmonary system of the patient to equilibrate, the VEMV-$CO_2$ value does not increase, then the prompted rate decreases again, for example to 6 ventilations per minute. A similar sequence may also be attempted for tidal volume, where the prompted tidal volume is decreased in a similar stepped sequence, for example from 600 ml to 500 ml then 400 ml. By progressively decreasing maximum ventilated lung volume, more space is provided for the heart to refill during the release phase of compressions, and may lead to a better balance between the amount of ventilatory gas delivered and blood flow from chest compressions.

In the ideal system, these two parameters will be individually adjusted for each patient. This can be achieved by using VEMV-$CO_2$ or $EtCO_2$ as the end parameter to optimize, with tidal volume, ventilation rate as potential intermediate parameters. If, for instance, the VEMV-$CO_2$ reaches the target level as a result of decreasing the ventilation rate or minute volume, and the compression depth is greater than 2 inches, then prompts to decrease compression depth may be provided to the rescuer.

FIG. 8B shows exemplary information displayed during the administration of ventilation to a patient. The user interface includes a $CO_2$ waveform 827. Additionally, the display can include other waveforms and relevant measured values such as respiration rate 840 and $SpO_2$ percentage 842.

A portion of the display can include ventilation information and provide guidance to the rescuer regarding proper ventilation. For example, the ventilation information can include a ventilation timer 822 (e.g., as described above in relation to FIG. 5) providing information about respiratory rate associated with the elapsed time between ventilations. Additionally, a portion of the display can include an indication 820 to change the rate of ventilation such as a message to ventilate faster or slower. In some examples, an audio indication can accompany the visual indicator to provide guidance to the rescuer.

Figure 10B:
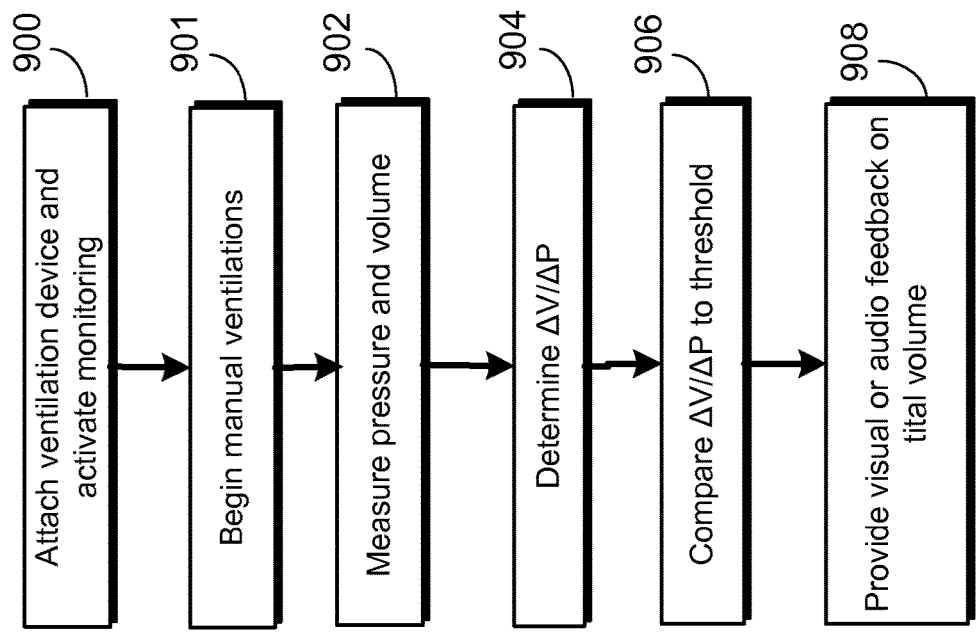
FIG. 10B is a flowchart of a process for providing feedback to a caregiver who is operating a ventilation bag or similar structure.
Figure 10A:
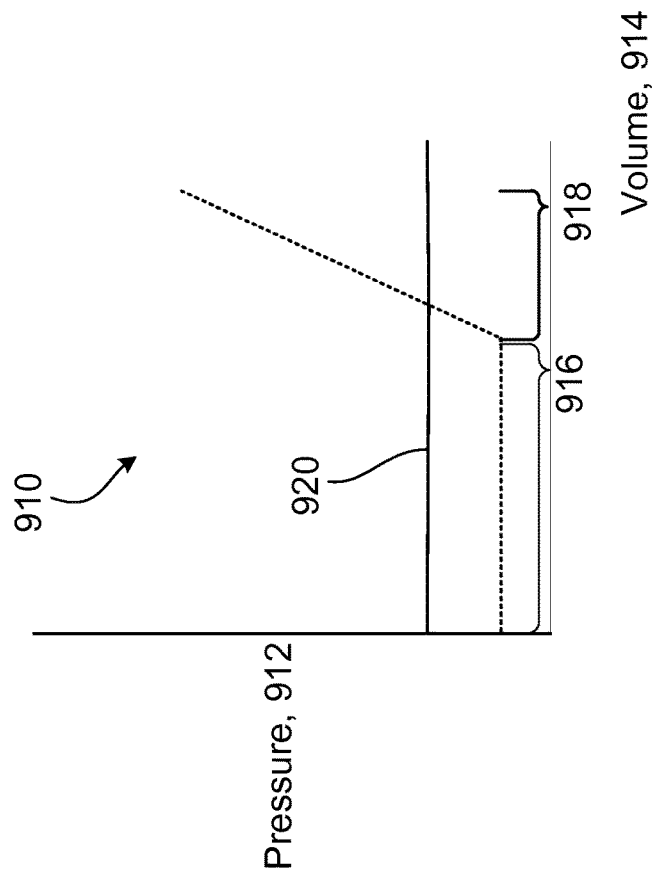
FIG. 10A shows an exemplary pressure versus volume graph.

FIG. 10A is an exemplary graph 910 of pressure versus volume during manual ventilation. Indications of pressure versus volume can be used as a guide for determining an optimal tidal volume for manual ventilation of victims. In general, for adult patients and older children tidal volume (Vt) is calculated in milliliters per kilogram and values in the range of 6 to 8 ml/kg are often used. Hence a patient weighing 70 kg would get a Vt of 420-480 ml. However, in the field, a rescuer often will not have access to patient weight to calculate a desired tidal volume. Thus, it can be beneficial to provide feedback to the rescuer on an appropriate tidal volume without performing calculations based on patient specific weight or age parameters.

In manual ventilation, as shown in FIG. 10A, as the amount volume of air administered to the victim increases, initially the pressure remains low and substantially constant (portion 916) as the lungs inflate. As the lungs near full inflation, the pressure required to administer additional volume is increased (portion 918). As the pressure rises above 45 cmH$_2$O (4.4 kPa) for adults, the risk of barotrauma is increased and efforts should be made to try to reduce the peak airway pressure. In infants and children it is lower levels of peak pressure may cause damage. In general, keeping peak pressures below 30 cmH$_2$O (2.9 kPa) is desirable. Thus, by observing changes in the observed or by observing changes in pressure per changes in volume, a determination can be made of when a desirable tidal volume has been administered to the victim.

The change in volume divided by change in pressure is sometimes referred to as a compliance measurement. Compliance is a measure of the "stiffness" of the lung and chest wall. The mathematical formula for compliance (C) is change in volume divided by change in pressure. The higher the compliance, the more easily the lungs will inflate in response to positive pressure. Compliance values can be calculated and used to provide feedback on tidal volume to the rescuer.

FIG. 10B is a flowchart of a process for providing feedback to a caregiver who is operating a ventilation bag or similar structure. In general, the process involves deploying various medical devices including a ventilation device at the scene of an emergency and providing feedback to the rescuer in relation to ventilation of a victim.

The process begins at box 900, where the rescuer attaches a ventilation bag to the victim and various sensors associated with the bag are activated. A communication link is also established between the sensor and a feedback unit, which may be in the form of a tablet, like tablet 116 in FIG. 1, or a defibrillator like defibrillator 112 in FIG. 1. The communication may occur automatically upon activating the two communicating components, such as by instigating an automatic BLUETOOTH or WiFi connection in a familiar manner.

At box 901, the rescuer begins manual ventilations. Such action may occur soon after rescuers, who may be lay rescuers using an AED or emergency medical technicians using an advanced defibrillator, arrive on a scene and recognize that a victim is in need of ventilation.

At box 902, ventilation data including pressure and volume are received from the ventilation device (e.g., using sensor devices described herein). Such information may be passed from the sensors to a computing component.

At box 904, the ventilation data is used to calculate a change in pressure per change in volume ($\Delta V/\Delta P$). An increased value for $\Delta V/\Delta P$ can indicate that the lung capacity has been reached and further air should not be administered to the victim during that manual ventilation cycle. At box 906, the measured $\Delta V/\Delta P$ value is compared to a threshold value and determinations may be made with respect to whether the ventilation is being properly or improperly applied relative to that protocol (e.g., a determination can be made regarding whether the rescuer is over-ventillating or underventillating the victim). The threshold is calculated individually for each patient. During the initial 150-500 ml of inspiratory volume, the Average Initial Compliance (AIP) is calculated. The ventilation is considered complete when the compliance has decreased to some predetermined fraction of the AIP, for example 25%.

Upon the device making such determinations, the device provides feedback to the rescuer in applying ventilation, as shown at box 908. For example, the feedback can be visual or audible feedback to guide a rescuer regarding whether to squeeze a ventilation bag more or less during a ventilation cycle. More particularly, if the comparison of the $\Delta V/\Delta P$ value to the threshold indicates that the lungs are not completely inflated (e.g., the $\Delta V/\Delta P$ value is less than the threshold indicating that the ventilation is likely in the flat portion 916), the rescuer can be advised to increase ventilation (e.g., by squeezing the bag to a greater extent). if the comparison of the $\Delta V/\Delta P$ value to the threshold indicates that the lungs are over inflated (e.g., the $\Delta V/\Delta P$ value is above the threshold indicating that the ventilation is likely in the sloped portion 918), the rescuer can be advised to decrease ventilation (e.g., by squeezing the bag to a lesser extent).

In some examples, the $\Delta P$ and $\Delta V$ measurements can be used to determine compliance features and determine a patient state based on the compliance features. Exemplary patient states that can be determined based on the compliance measurements include barotraumas, hemothorax, pneumothorax, intubation in mainstem, flail chest, and/or pediatric lung overdistension. AIPs for healthy adult patients are approximately 300 ml/cmH2O; AIPs below about 150 ml/cmH2O may indicate one of the above conditions. In some additional examples, the compliance measurement can be used to detect overdistension of lungs during pediatric ventilation to provide information related to for appropriate lung ventilation volume for a pediatric patient.

Figure 10C:
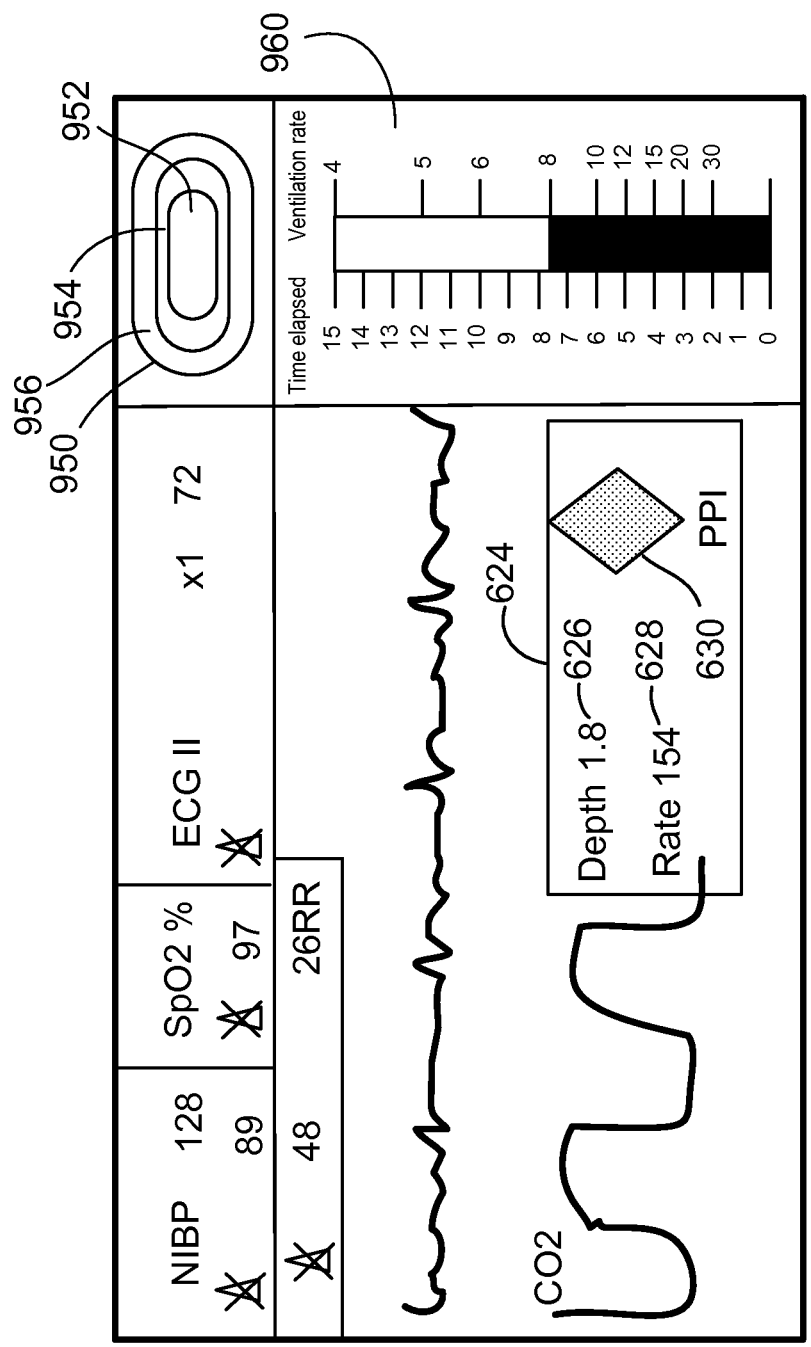
FIG. 10C shows an example of a visual feedback provided to a caregiver.

FIG. 10C shows exemplary information displayed during the administration of ventilation and CPR compressions to a patient. The display can include information such as a ventilation timer 960 (e.g., as described above in relation to FIG. 5) and other observed values (e.g., as also described above in relation to FIG. 5).

Additionally, a portion of the display can include information related to the tidal volume. In the example shown in FIG. 10C, this information can be displayed in the form of a shape representing a ventilation bag with three portions 952, 954, and 956 representing under-ventilation, appropriate ventilation, and over-ventilation, respectively. An indicator can be provided to show the extent to which a rescuer is squeezing the ventilation bag such that the rescuer can aim to keep the indicator within the appropriate ventilation range 954. Other indicators such as text based or audio indicators can also be provided. In some examples, a two dimensional indicator may be provided by augmenting a feedback graphic for a parameter such as rate as FIG. 5, to graphically represent tidal volume as a second graphical feature of the bar, for instance the width of the bar. The color of the bar may also be used as a graphical indication, for instance a three color bar, with yellow representing a tidal volume that is too low, green as correct within a range of +/−20 of desired range, and red indicating too much volume. During the course of each ventilation the color of the bar will start as yellow, then progress to green when in the appropriate range. If the rescuer continues squeezing the bag and delivers too much gas, the color of the bar will change to red.

In some examples, in addition to or instead of determining the appropriate tidal volume based on change in pressure and change in volume measurements from the ventilation device 700, the tidal volume can be computed based on one or more of a patient's height, girth, weight and gender. This information can be determined automatically or can be input into the computing device by the rescuer. For example, the information can be input using a tablet PC, determined based on information collected by an accelerometer, or received from an automatic defibrillation and compression device configured to obtain a measure of patient circumference. In some additional examples, the system is configured to calculate the estimate thoracic volume based on a measured ventilation tidal volume and an instantaneous lung volume.

In some situations, a rescuer may have difficulty forming a leak tight seal between the ventilation device such that air from the bag leaks into the atmosphere rather than being directed into the victim's lungs. In other situations, a rescuer may provide an appropriate tidal volume of air to the patient, but the rescuer may not fully release the ventilation bag causing the air to remain in the victim's lungs rather than being fully exhaled. It can be beneficial to detect such situations where air is not being appropriately inhaled or exhaled so that the rescuer can be informed that the ventilation is sub-optimal.

Figure 11:
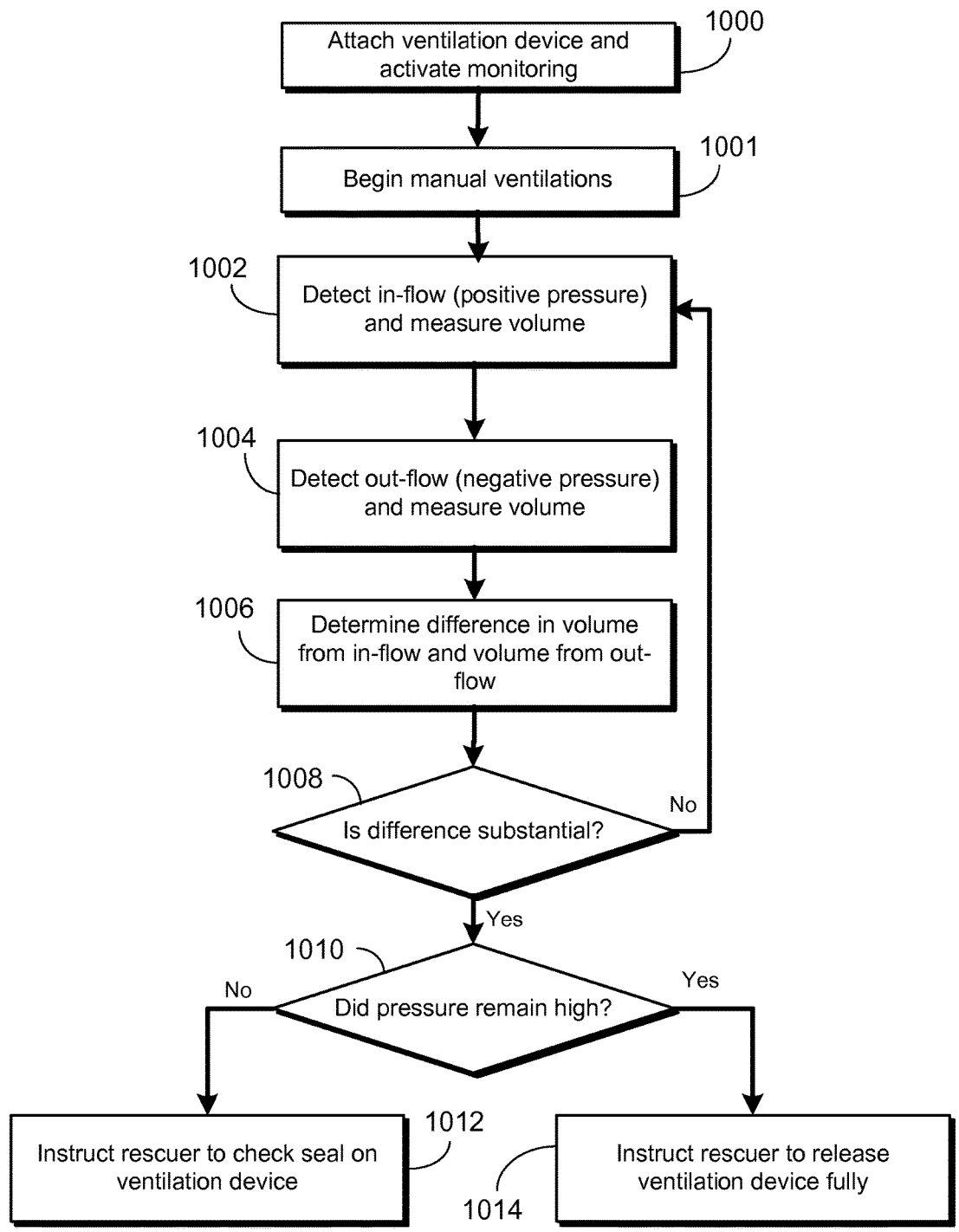
FIG. 11 is a flowchart of a process for providing feedback to a caregiver who is operating a ventilation bag or similar structure.

FIG. 11 is a flowchart of a process for providing feedback to a caregiver who is operating a ventilation bag or similar structure. In general, the process involves deploying various medical devices including a ventilation device at the scene of an emergency and providing feedback to the rescuer in relation to ventilation of a victim.

The process begins at box 1000, where the rescuer attaches a ventilation bag to the victim and various sensors associated with the bag are activated. A communication link is also established between the sensor and a feedback unit, which may be in the form of a tablet, like tablet 116 in FIG. 1, or a defibrillator like defibrillator 112 in FIG. 1. The communication may occur automatically upon activating the two communicating components, such as by instigating an automatic BLUETOOTH or WiFi connection in a familiar manner.

At box 1001, the rescuer begins manual ventilations. Such action may occur soon after rescuers, who may be lay rescuers using an AED or emergency medical technicians using an advanced defibrillator, arrive on a scene and recognize that a victim is in need of ventilation.

At boxes 1002 and 1004, ventilation data including pressure and volume are received from the ventilation device (e.g., using sensor devices described herein). Such information may be passed from the sensors to a computing component. More particularly, at box 1002, the ventilation data is used to detect an in-flow of air and measure the volume of air that is provided from the ventilation bag. At box 1004, the ventilation data is used to detect an out-flow of air and measure the volume of air that is provided from the victim during an exhale.

At box 1006, the ventilation data is used to calculate the difference between the in-flow volume and the out-flow volume. A greater in-flow volume than out-flow volume can indicate that either the rescuer has not fully released the ventilation bag allowing the victim to exhale all air from the lungs or that the seal between the ventilation device and the victim is not leak-tight and a significant amount of air exiting the ventilation device is not being forced into the patient's lungs.

At box 1008, the calculation results are compared to a threshold to determine if the difference between in-flow volume and out-flow volume is significant. If not, the process returns to step 1002. If the difference is significant, for example greater than 15%-25% (e.g., 20%), the system determines if the pressure remained high during the entire ventilation cycle. If the pressure remained high, then the difference in volume is likely due to the rescuer not fully releasing the ventilation bag such that the victim is unable to exhale all air from the lungs. In this case, as shown in box 1014, the system instructs the rescuer to fully release the ventilation device. If the pressure did not remain high, then the difference is volume is likely due to the air leaking from the ventilation device rather than being fully delivered to the victim's lungs. In this case, as shown in box 1012, the system instructs the rescuer to check the seal between the victim and the ventilation device.

In some examples, it can be beneficial to determine when a victim to whom manual ventilation is being delivered has taken a spontaneous breath. For example, if the victim is taking spontaneous breaths, it may be desirable to discontinue manual ventilation or to provide medication to suppress spontaneous breathing.

Figure 12:
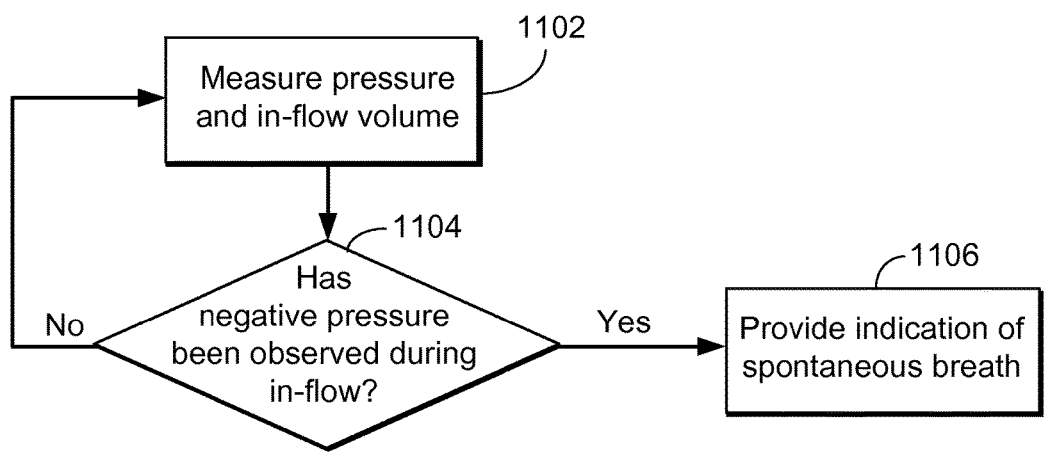
FIG. 12 is a flowchart of a process for providing feedback to a caregiver who is operating a ventilation bag or similar structure.

FIG. 12 is a flowchart of a process for providing feedback to a caregiver who is operating a ventilation bag or similar structure. In general, the process involves deploying various medical devices including a ventilation device at the scene of an emergency and providing feedback to the rescuer in relation to whether the victim has taken a spontaneous breath.

After, the rescuer attaches a ventilation bag to the victim and various sensors associated with the bag are activated and the rescuer begins manual ventilations, at box 1102, ventilation data including pressure and volume are received from the ventilation device (e.g., using sensor devices described herein). Such information may be passed from the sensors to a computing component. At box 1104, the ventilation data is used to determine if a negative pressure has been observed during an in-flow of air to the patient. In general, manual ventilation results in a positive pressure during an air in-flow cycle while spontaneous breaths result in a negative pressure during an air in-flow cycle. If a negative pressure is observed during an air in-flow cycle, at box 1106, the system notifies the rescuer (via a visual or audio indicia) that a spontaneous breath has been observed. Additionally or alternatively, the system can provide a message indicating potential return of spontaneous circulation (ROSC) based on the detection of a spontaneous breath.

In some examples, information from the ventilation assembly 700 can be used to calculate a single value that provides a measure of the squareness of the complete breath cycle or steepness of the expiratory portion of the breath cycle of the spirometry curve. Spirometry is helpful in diagnosing and treating patients with dyspnea (difficulty breathing) such as asthma, pulmonary fibrosis, cystic fibrosis, heart failure and COPD. Forced Vital Capacity (FVC) and Forced Expiratory Volume in 1 second (FEV1) are measured and the ratio of these two measures, FEV1/FVC is calculated (referred to as FEV1%). In obstructive pulmonary diseases such as asthma, emphysema, COPD or chronic bronchitis, FEV1 decreases due to higher airway resistance to expiratory flow and the FVC may be decreased, as opposed to restrictive diseases such as pulmonary fibrosis where the FEV1 and FVC are both reduced and the ratio may be similar to healthy individuals. The spirometry measures and calculations are therefore believed to be helpful in the differential diagnosis of dyspnea. This value can be displayed to a rescuer on a user display device.

In some additional examples, the system generates an estimate of a thoracic state impedance based on an estimate of lung volume. The estimate of lung volume can be determined using one or more of the processes described herein. The estimate of thoracic state impedance can be provided to an adaptive filter and the system can filter ventilation-induced artifacts in the transthoracic impedance signal to provide a more accurate estimate of the impedance changes induced by cardiac output for the impedance cardiography (ICG) signal.

In some examples, an adaptive filter may be used to filter out artifact in the impedance cardiographic (ICG) signal introduced by ventilations or breathing. An exemplary filter can be based on the function:

Adaptive filter–$z[i]=w[i]*x[i]$

System Estimation–$w[i]=w[i-1]+e[i-1]*a[i]$

Figure 13A:
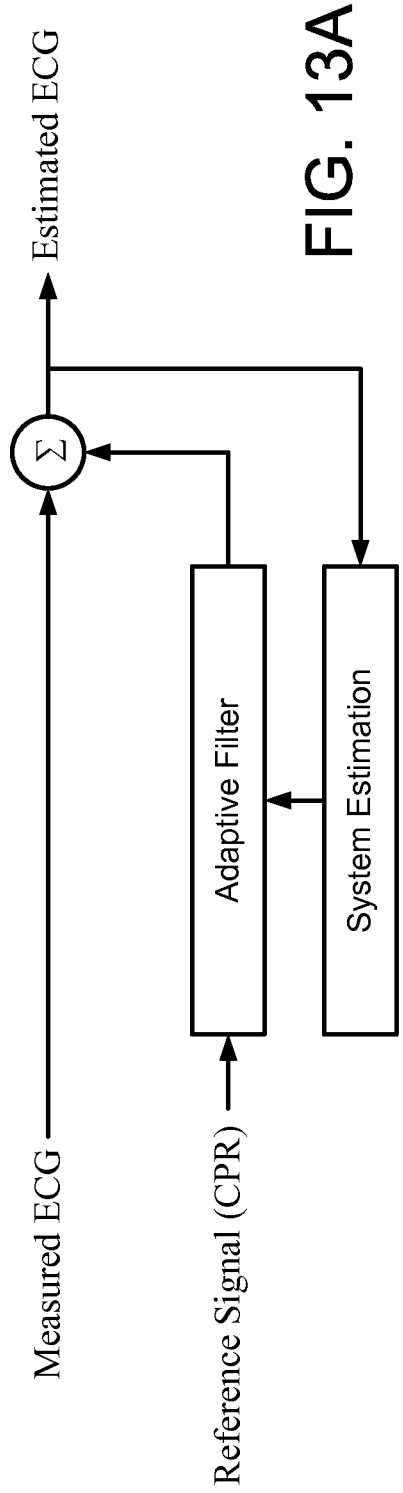
FIGS. 13A and 13B are diagrams of exemplary filters.
Figure 13B:
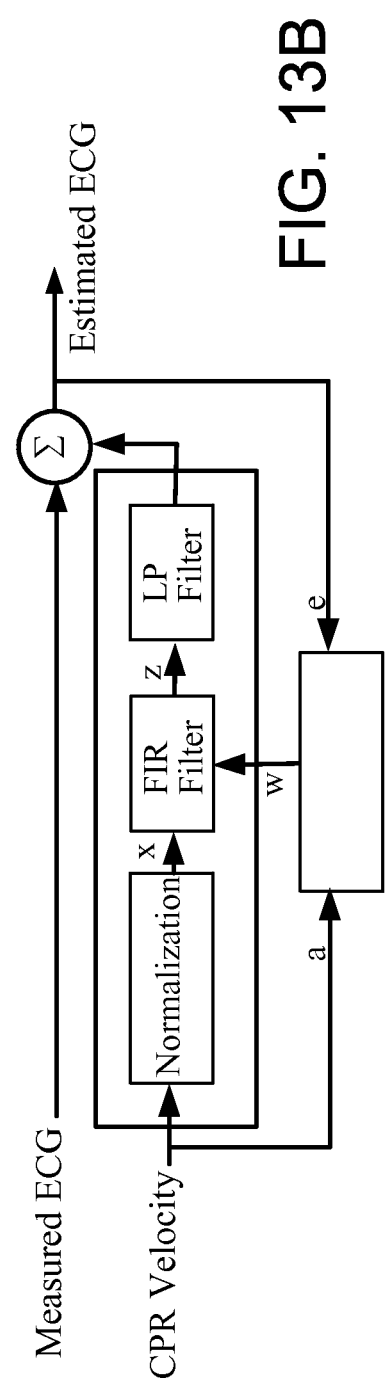
Figure 14:
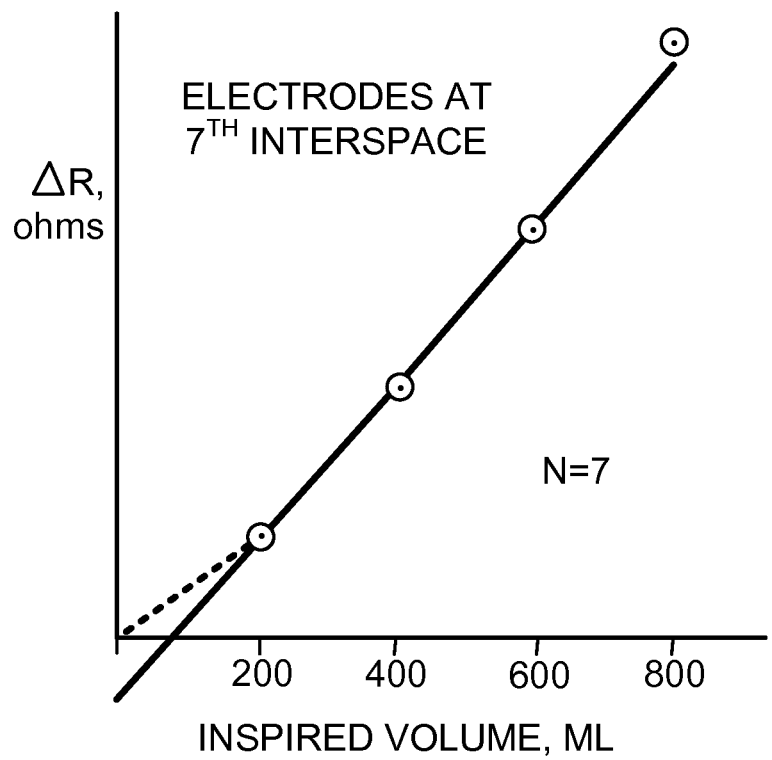
FIG. 14 is a graph of a change in resistance per volume.

Referring to FIGS. 13A and 13B, the Reference Signal is provided by the ventilatory volume measured. The system employed here is a first-order system, though more complex forms may be implemented, such as higher order adaptive filters, Kalman filters, Particle filters, etc. Because there is very little phase lag between the lung volume and transthoracic impedance, an even simpler system may be implemented that generates a transfer function to compute impedance as a function of lung volume based on 3-10 ventilations. Instantaneous measured lung volume is the input to the transfer function and the result is subtracted from the transthoracic impedance signal to filter out artifact due to lung volume changes. As can be seen from FIG. 14, the transfer function will often have a non-linearity, with lower gain in the 0-200 ml of lung volume region. This can be compensated for with standard techniques in the transfer function.

In some embodiments, it can be beneficial to time the CPR compressions such that the CPR compression does not occur at the same time as a ventilation. In order to time the compressions, the system includes a sensor such as an accelerometer or pressure sensor that detects manual or mechanical CPR compressions. Based on information from the accelerometer or pressure sensor in combination with data from the ventilation assembly 700, the system determines whether a timing for a ventilation overlaps with a timing for a CPR compression cycle and provides an indication to the rescuer if a ventilation is being delivered during a compression cycle so the rescuer can delay either the compression or the ventilation so that they do not overlap.

In another implementation, the pressure sensor 21 can be combined with a second sensor, such as accelerometer 76, to detect the common clinical situation in which the intubation tube, commonly called the endotracheal (ET) tube, has been improperly positioned into the stomach via the esophagus, rather than into the lungs via the trachea. It is also not uncommon for the ET tube to become dislodged during the course of resuscitation, or as a result of vibrations during transport by ambulance or other mode of transportation. Detection of a pressure waveform pulse is used to initiate an analysis of either the accelerometer waveform, the TTI waveform, or both to see if the attempt to deliver respiratory gas via ventilation is delivering the gas to the lungs or to the stomach (via the esophagus). If the gas is delivered to the lungs, there will be an associated pulse waveform of the actual measured displacement of the sternal region where the accelerometer is placed (double integration of the accelerometer waveform will show a rising sternum). Alternatively, a TTI measurement can be used, as air delivered to the lungs will cause a rise in transthoracic impedance (TTI). Due to both the compressible nature of the gas as well as the fact that the lungs expand both sternally and diaphragmatically, there will be some delay following generation of the pressure pulse before the associated displacement waveform is observed from the accelerometer or the TTI measurement.

In some implementations, two pulse detection methods are used. The first time aligns the pressure waveform pulse with the pulse waveform of the sternal displacement and TTI measurement. If the delay from the leading edge of the pressure pulse waveform to the leading edge of the displacement and TTI waveforms is less than 700 milliseconds, and the delay of the trailing edge of the pressure pulse waveform to the trailing edge of the displacement and TTI waveforms is also less than 700 milliseconds, then the displacement and TTI pulse waveforms are considered to be as a result of the ventilation cycle. The second pulse detection method uses the acceleration waveform to detect the first initial movement of the sternum due to the ventilation. The displacement waveform is calculated, and the first pulse of the acceleration signal that contributes to the displacement pulse determines the start of the sternal displacement pulse. A more accurate onset of motion of the sternum due to ventilation can oftentimes be achieved in this manner.

If the displacement and TTI waveforms are found to be the result of the ventilation pressure waveform pulse, then the ET tube is considered to be in the proper location in the trachea and not in the esophagus. A visual indicator can provide visual feedback to the rescuer as to whether or not the ET tube has been properly placed.

Figure 15:
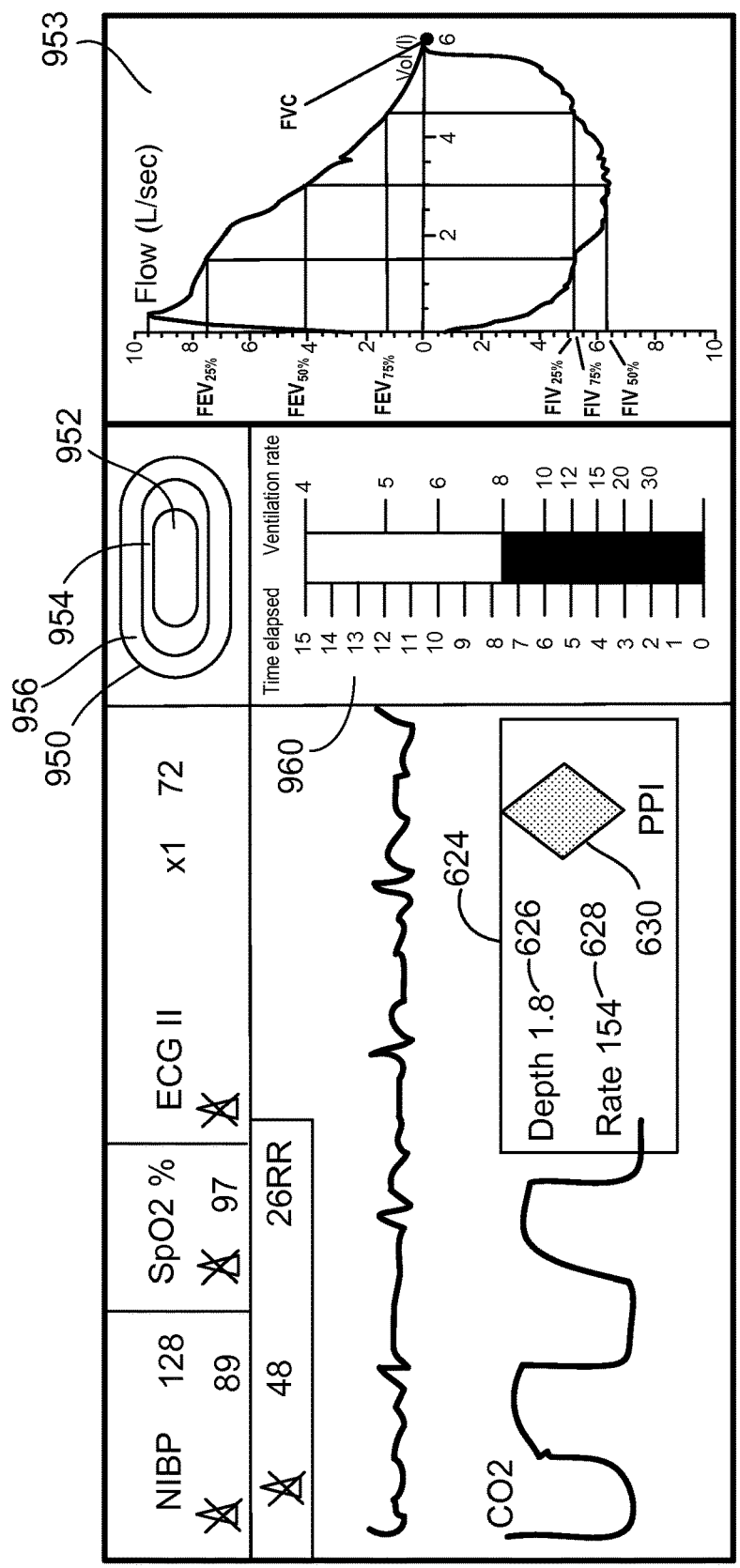
FIG. 15 shows an example of a visual feedback provided to a caregiver.

As described herein, based on multiple different sensors in the ventilation device various types of feedback can be provided to a rescuer about the ventilation of a victim. In some examples, multiple different feedbacks related to ventilation can be presented to a rescuer on a single user interface. An example of such a collection of ventilation related information is shown in FIG. 15. As shown in FIG. 15, in addition to the components discussed above in relation to FIG. 10C, the user interface can include a spirometry graph 953. The spriometry graph 953 can display a flow-volume loop, which graphically depicts the rate of airflow on the Y-axis and the total volume inspired or expired on the X-axis. Other components, for example, such as those discussed herein can additionally or alternatively be included in the ventilation user interface.

Figure 16:
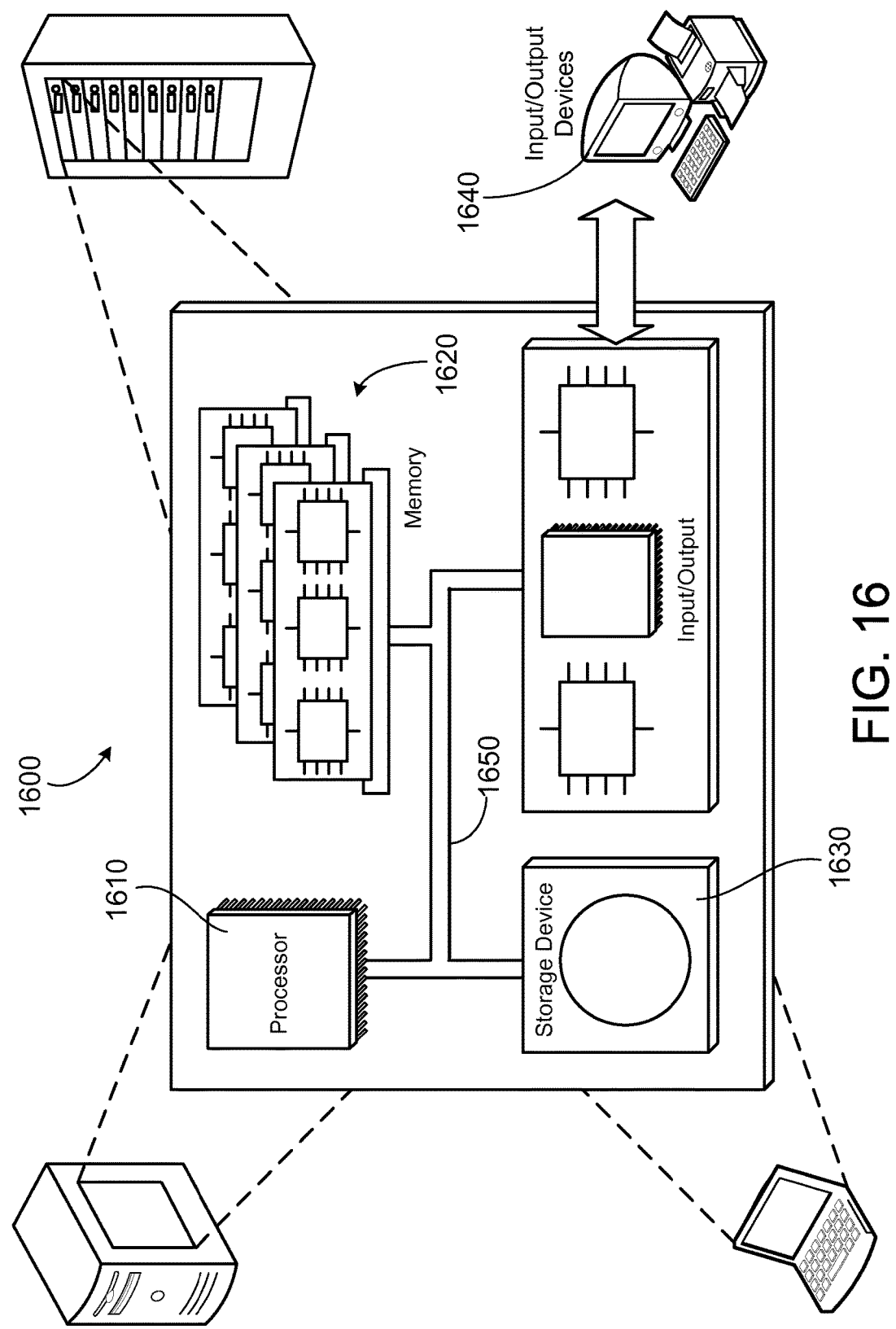
FIG. 16 is a schematic diagram of a general computing system that can be employed to operate a medical device in manners like those discussed here.

FIG. 16 is a schematic diagram of a computer system 1300. The system 1300 can be used for the operations described in association with any of the computer-implement methods described previously, according to one implementation. The system 1300 is intended to include various forms of digital computers, such as laptops, desktops, workstations, personal digital assistants, servers, blade servers, mainframes, and other appropriate computers. The system 1300 can also include mobile devices, such as personal digital assistants, cellular telephones, smartphones, and other similar computing devices. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 1300 includes a processor 1310, a memory 1320, a storage device 1330, and an input/output device 1340. Each of the components 1310, 1320, 1330, and 1340 are interconnected using a system bus 1350. The processor 1310 is capable of processing instructions for execution within the system 1300. The processor may be designed using any of a number of architectures. For example, the processor 1310 may be a CISC (Complex Instruction Set Computers) processor, a RISC (Reduced Instruction Set Computer) processor, or a MISC (Minimal Instruction Set Computer) processor.

In one implementation, the processor 1310 is a single-threaded processor. In another implementation, the processor 1310 is a multi-threaded processor. The processor 1310 is capable of processing instructions stored in the memory 1320 or on the storage device 1330 to display graphical information for a user interface on the input/output device 1340.

The memory 1320 stores information within the system 1300. In one implementation, the memory 1320 is a computer-readable medium. In one implementation, the memory 1320 is a volatile memory unit. In another implementation, the memory 1320 is a non-volatile memory unit.

The storage device 1330 is capable of providing mass storage for the system 1300. In one implementation, the storage device 1330 is a computer-readable medium. In various different implementations, the storage device 1330 may be a floppy disk device, a hard disk device, an optical disk device, or a tape device.

The input/output device 1340 provides input/output operations for the system 1300. In one implementation, the input/output device 1340 includes a keyboard and/or pointing device. In another implementation, the input/output device 1340 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semi-conductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

A number of embodiments have been described. Nevertheless, it will be understood that various modifications may be made without departing from the spirit and scope of the invention. Accordingly, other embodiments are within the scope of the following claims.

What is claimed is:

1. A system for providing feedback on delivery of cardiopulmonary resuscitation (CPR), the system comprising:
   a manual patient ventilation unit defining an airflow path, the unit arranged so that when the unit is applied to a patient, the airflow path is in fluid communication with the patients airway, the patient ventilation unit comprising:
      a ventilation bag configured to enable manual ventilation of the patient by a rescuer;
      at least one first sensor in the airflow path positioned to sense the presence of ventilation airflow and measure a gas flow rate in the airflow path; and
      at least one second sensor in the airflow path positioned to sense gas pressure in the airflow path;
   at least one chest compression sensor configured to detect and measure compression information based on chest compressions applied to the patient; and
   a feedback unit separate from the manual patient ventilation unit comprising a processor arranged to:
      wirelessly receive data generated by the at least one first sensor and the at least one second sensor;
      determine one or more ventilation quality parameters based at least in part on a gas flow volume calculated based on the sensed gas flow rate and gas pressures;
      receive compression data generated by the at least one chest compression sensor;
      determine one or more chest compression parameters based at least in part on the measured compression information; and
      provide both ventilation feedback and chest compression feedback to a rescuer, the ventilation feedback comprising the one or more ventilation quality parameters and instructions for performing ventilations based upon a comparison of the ventilation quality parameters with a ventilation protocol comprising ranges of predetermined acceptable values for administering ventilations to the patient and the chest compression feedback comprising the one or more chest compression parameters and instructions for performing chest compressions based upon a comparison of the chest compression parameters with a chest compression protocol comprising ranges of predetermined acceptable values for administering chest compressions to the patient, wherein the ventilation quality parameters comprise one or more of tidal volume, minute volume, end-inspiratory pressure, and maximum ventilation pressure.

2. The system of claim 1, further comprising circuitry configured for delivery of electromagnetic stimulation to the patient.

3. The system of claim 1, wherein the ventilation bag comprises a flexible reservoir containing ventilatory gases configured to enable manual ventilation of the patient by a rescuer squeezing the flexible reservoir.

4. The system of claim 1, wherein the ventilation bag is configured to enable manual ventilation of the patient by a rescuer pressing a switch of an electromechanically-controlled ventilator.

5. The system of claim 1, wherein the one or more ventilation quality parameters include an indicator indicative of a ventilation being delivered during a compression cycle.

6. The system of claim 1, further comprising a capnometer in the airflow path positioned to sense the concentration of $CO_2$ in the airflow path.

7. The system of claim 1, further comprising an oxygen sensor in the airflow path positioned to sense the concentration of $O_2$ in the airflow path.

8. The system of claim 1, wherein:
the processor is configured to compute end-tidal $CO_2$ values; and
the feedback unit is configured to provide an indication to increase ventilation if the end-tidal $CO_2$ value is outside of a first range and to decrease ventilation if the end-tidal $CO_2$ value is outside of a second range.

9. The system of claim 1, wherein:
the processor is further configured to compute volumetric $CO_2$ values; and
the feedback unit is configured to provide an indication to increase ventilation if the volumetric $CO_2$ value is outside of a first range and to decrease ventilation if the volumetric $CO_2$ value is outside of a second range.

10. The system of claim 1, wherein the processor is further configured to compute lung compliance.

11. The system of claim 10, wherein the processor is further configured to detect at least one of the following conditions based, at least in part, on the lung compliance measurements: barotrauma, hemothorax, pneumothorax, intubation in the mainstem, flail chest, or pediatric lung distension.

12. The system of claim 10 wherein the feedback unit is configured to provide feedback related to tidal volume.

13. The system of claim 1, wherein:
the processor is configured to compute a difference in in-flow volume and out-flow volume; and
the feedback unit is configured to provide feedback related one or more of ventilation release and ventilation seal.

14. The system of claim 1, wherein:
the processor is configured to identify conditions when a negative pressure occurs during in-flow of air; and
the feedback unit is configured to provide feedback regarding the existence of a spontaneous breath when a negative pressure occurs during in-flow of air.

15. The system of claim 1, wherein the feedback comprises feedback that communicates to the rescuer an appropriate volume for providing ventilation to the patient.

16. The system of claim 1, wherein the feedback unit comprises a visual feedback mechanism for providing information to a rescuer regarding delivery of ventilation comprising a plurality of lights arranged to indicate, based on which lights of the plurality of lights are activated, whether excessive ventilation, too little ventilation, or an appropriate amount of ventilation is being provided to the victim.

17. The device of claim 1, wherein the feedback unit is configured to provide an instruction pertaining to varying the delivered tidal volume.

18. The system of claim 1, wherein the feedback unit comprises a visual feedback mechanism for providing information to a rescuer regarding delivery of ventilation comprising a ventilation timer providing information about respiratory rate.

19. The system of claim 1, wherein the feedback unit comprises a visual feedback mechanism for providing information to a rescuer regarding delivery of ventilation comprising a ventilation timer providing information about elapsed time between ventilation events.

20. The system of claim 1, wherein the feedback unit comprises a device configured to form audible prompts and the feedback comprises audible prompts.

21. The system of claim 1, wherein the feedback unit comprises a device configured to form audible prompts and the feedback comprises verbal instructions.

22. The system of claim 1, wherein the feedback unit comprises a device configured to form audible prompts and the feedback comprises one or more tones.

23. The system of claim 1, wherein the feedback unit comprises a graphical display and the feedback comprises visual feedback for the one or more ventilation parameters and the one or more chest compression parameters provided on the graphical display.

24. The system of claim 1, wherein the feedback unit comprises a graphical display and the feedback comprises a visual representation of a shape with demarcations indicating specific tidal volume values, wherein the volume fills during the ventilation.

25. The system of claim 24, wherein the visual representation further comprises a visual marker indicative of a target tidal volume.

26. The system of claim 1, wherein the processor is further configured to determine compliance features and determine a patient state based on the compliance features.

27. The system of claim 26, wherein the patient state comprises a state selected from the group consisting of barotraumas, hemothorax, pneumothorax, intubation in mainstem, flail chest, and pediatric lung overdistension.

28. The system of claim 1, wherein the processor is further configured to detect a mask leak.

29. The system of claim 1, wherein the processor is further configured to compare pressure data from the at least one second sensor and flow data from the at least one first sensor at multiple points in time to compute an estimate of lung compliance.

30. The system of claim 29, wherein the processor is further configured to detect overdistension of lungs during pediatric ventilation based on the estimate of compliance and the feedback unit is further configured to provide information related to for appropriate lung ventilation volume for a pediatric patient.

31. The system of claim 1, wherein the processor is configured to detect a spontaneous breath based on information related to a negative pressure combined with inspiratory flow.

32. The system of claim 31, wherein the feedback unit is configured to provide a message indicating potential return of spontaneous circulation (ROSC) based on the detection of a spontaneous breath.

33. The system of claim 1, wherein the processor is further configured to:
generate an estimate of lung volume;
generate an estimate of a thoracic state impedance based on the estimate of lung volume;
provide the estimate of thoracic state impedance to an adaptive filter; and
filter ventilation-induced artifacts in the transthoracic impedance signal to generate an estimate of the impedance changes induced by cardiac output.

34. The system of claim 1, wherein the feedback unit is configured to provide a simultaneous display of flow rate and volume.

35. The system of claim 1, wherein the feedback comprises a graphical plot.

36. The system of claim 1, wherein the feedback comprises side-by-side numerics, the numerics comprising at least one numeric representative of the one or more ventilation parameters and a second numeric representative of the one or more chest compression parameters.

37. The system of claim 1, wherein the feedback comprises spirometery data for one or more of oxygen, carbon dioxide, overall gas volume and rate.

38. The system of claim 1, wherein the feedback comprises a value indicative of a measure of the squareness of a spirometry curve.

39. The system of claim 1, wherein the processor is further configured to:
receive information related to two or more of a patient's height, girth, weight and gender; and
calculate an estimate thoracic volume based on the two or more of the patient's height, girth, weight and gender.

40. The system of claim 39, wherein the processor is further configured to receive the information related to two or more of the patient's height, girth, weight and gender from a tablet PC.

41. The system of claim 39, wherein the processor is further configured to receive the information related to two or more of the patient's height, girth, weight and gender from an accelerometer.

42. The system of claim 39, wherein the processor is further configured to receive the information related to two or more of the patient's height, girth, weight and gender from an automatic defibrillation and compression device configured to obtain a measure of patient circumference.

43. The system of claim 39, wherein the processor is further configured to calculate the estimate thoracic volume based on a measured ventilation tidal volume and an instantaneous lung volume.

44. The system of claim 1, wherein the patient ventilation unit comprises a handheld breathing tube.

45. The system of claim 1, wherein the patient ventilation unit comprises a mouthguard configured to fit between the patient's lips and teeth and to provide a seal between the ventilation unit and the patient.

46. The system of claim 1, wherein the patient ventilation unit comprises a mask that seals to and fits over a lower portion of the patient's face.

47. The system of claim 1, wherein the at least one first sensor comprises a differential pressure sensor.

48. A system for providing feedback on delivery of cardiopulmonary resuscitation (CPR), the system comprising:
a manual patient ventilation unit defining an airflow path, the unit arranged so that when the unit is applied to a patient, the airflow path is in fluid communication with the patient's airway, the patient ventilation unit comprising;
a ventilation bag configured to enable manual ventilation of the patient by a rescuer;
at least one first sensor in the airflow path positioned to sense the presence of ventilation airflow and measure a gas flow rate in the airflow path; and
at least one second sensor in the airflow path positioned to sense gas pressure in the airflow path;
at least one chest compression sensor configured to detect and measure compression information based on chest compressions applied to the patient; and
a feedback unit separate from the manual patient ventilation unit comprising a processor arranged to:
wirelessly receive data generated by the at least one first sensor and the at least one second;
determine an instantaneous lung compliance measurement based at least in part on a gas flow volume calculated based on the sensed gas flow rate and gas pressures;
receive compression data generated by the at least one chest compression sensor;
determine one or more chest compression parameters based at least in part on the measured compression information; and
provide both ventilation feedback and chest compression feedback to a rescuer by the feedback unit, the ventilation feedback comprising the instantaneous lung compliance measurement and instructions for performing ventilations based upon a comparison of the instantaneous lung compliance measurement with a ventilation protocol comprising a range of predetermined acceptable instantaneous lung compliance values for administering ventilations to the patient and the chest compression feedback comprising the one or more chest compression parameters and instructions for performing chest compressions based upon a comparison of the chest compression parameters with a chest compression protocol comprising ranges of predetermined acceptable values for administering chest compressions to the patient.

49. The system of claim 48, wherein the processor is further configured to detect at least one of the following conditions based, at least in part, on the instantaneous lung compliance measurements: barotrauma, hemothorax, pneumothorax, intubation in the mainstem, flail chest, or pediatric lung distension.

50. The system of claim 48, wherein the processor is further configured to detect overdistension of lungs during pediatric ventilation based on the estimate of instantaneous lung compliance and the feedback unit is further configured to provide information related to for appropriate lung ventilation volume for a pediatric patient.

51. The system of claim 48, wherein the processor is further configured to determine a patient state based on the instantaneous lung compliance measurement.

52. The system of claim 51, wherein the patient state comprises a state selected from the group consisting of barotraumas, hemothorax, pneumothorax, intubation in mainstem, flail chest, and pediatric lung overdistension.

53. The system of claim 48, wherein the feedback comprises spirometery data for one or more of oxygen, carbon dioxide, overall gas volume and rate.

54. The system of claim 48, wherein the feedback comprises a value indicative of a measure of the squareness of a spirometry curve.

55. The system of claim 1, wherein the chest compression feedback further comprises information about an effectiveness of chest compressions based on both the one or more ventilation quality parameters and the one or more chest compression parameters.

56. The system of claim 48, wherein the chest compression feedback further comprises information about an effectiveness of the chest compressions based on the instantaneous lung compliance measurement and the one or more chest compression parameters.

57. The system of claim 1, wherein at least one first sensor comprises an airflow sensor positioned in the airflow path and the at least one second sensor comprises a pressure sensor positioned in the airflow path.

58. The system of claim 48, wherein at least one first sensor comprises an airflow sensor positioned in the airflow path and the at least one second sensor comprises a pressure sensor positioned in the airflow path.

* * * * *

UNITED STATES PATENT AND TRADEMARK OFFICE
CERTIFICATE OF CORRECTION

PATENT NO. : 10,137,265 B2
APPLICATION NO. : 13/473002
DATED : November 27, 2018
INVENTOR(S) : Gary A. Freeman et al.

Page 1 of 1

It is certified that error appears in the above-identified patent and that said Letters Patent is hereby corrected as shown below:

In the Claims

Column 30, Line 40, Claim 1, delete "patients" and insert -- patient's --

Column 33, Line 34, Claim 37, delete "spirometery" and insert -- spirometry --

Column 34, Line 12-13, Claim 48, delete "comprising;" and insert -- comprising: --

Column 35, Line 6, Claim 53, delete "spirometery" and insert -- spirometry --

Signed and Sealed this
Second Day of April, 2019

Andrei Iancu
*Director of the United States Patent and Trademark Office*